(12) United States Patent
Hirose et al.

(10) Patent No.: US 10,782,501 B2
(45) Date of Patent: Sep. 22, 2020

(54) MEDICAL OBSERVATION DEVICE

(71) Applicants: SONY OLYMPUS MEDICAL SOLUTIONS INC., Tokyo (JP); SONY CORPORATION, Tokyo (JP)

(72) Inventors: Kenji Hirose, Tokyo (JP); Tetsuharu Fukushima, Tokyo (JP); Atsushi Miyamoto, Kanagawa (JP); Wataru Kokubo, Tokyo (JP); Toshimitsu Tsuboi, Tokyo (JP)

(73) Assignees: SONY OLYMPUS MEDICAL SOLUTIONS INC., Tokyo (JP); SONY CORPORATION, Tokyo (JP)

( * ) Notice: Subject to any disclaimer, the term of this patent is extended or adjusted under 35 U.S.C. 154(b) by 410 days.

(21) Appl. No.: 15/328,181

(22) PCT Filed: Jul. 23, 2015

(86) PCT No.: PCT/JP2015/071009
§ 371 (c)(1),
(2) Date: Jan. 23, 2017

(87) PCT Pub. No.: WO2016/017532
PCT Pub. Date: Feb. 4, 2016

(65) Prior Publication Data
US 2017/0176704 A1    Jun. 22, 2017

(30) Foreign Application Priority Data
Aug. 1, 2014    (JP) .................................. 2014-157288

(51) Int. Cl.
*G02B 7/00* (2006.01)
*A61B 90/20* (2016.01)
(Continued)

(52) U.S. Cl.
CPC .............. *G02B 7/001* (2013.01); *A61B 90/20* (2016.02); *A61B 90/25* (2016.02);
(Continued)

(58) Field of Classification Search
None
See application file for complete search history.

(56) References Cited

U.S. PATENT DOCUMENTS 6,216,056 B1    4/2001    Ito et al.
7,386,365 B2 *  6/2008    Nixon .................... B25J 9/1692
                                                            700/245
(Continued)

FOREIGN PATENT DOCUMENTS

EP    0 849 053 A1    6/1998
JP    8-266555 A      10/1996
(Continued)

OTHER PUBLICATIONS

Combined Chinese Office Action and Search Report dated Sep. 30, 2018 in corresponding Patent Application No. 201580041546.4 (with English Translation), 13 pages.
(Continued)

*Primary Examiner* — Chikaodili E Anyikire
(74) *Attorney, Agent, or Firm* — Xsensus LLP

(57) ABSTRACT

A medical observation device includes an imaging unit configured to photograph an image of an operation site, and a holding unit configured to be connected with the imaging unit and have rotary shafts which are operable with at least six degrees of freedom. Among the rotary shafts, at least two shafts are active shafts whose driving is controlled based on states of the rotary shafts, and at least one shaft is a passive shaft which is rotated according to direct external manipulation accompanying contact.

20 Claims, 11 Drawing Sheets

(51) Int. Cl.
*A61B 90/25* (2016.01)
*G02B 21/00* (2006.01)
*G02B 21/36* (2006.01)
*G03B 13/36* (2006.01)
*H04N 5/232* (2006.01)
*B25J 9/16* (2006.01)
*G05B 19/423* (2006.01)

(52) U.S. Cl.
CPC ....... G02B 21/0012 (2013.01); G02B 21/362 (2013.01); G03B 13/36 (2013.01); H04N 5/23296 (2013.01); B25J 9/1633 (2013.01); G05B 19/423 (2013.01)

(56) References Cited

U.S. PATENT DOCUMENTS

| | | | |
|---|---|---|---|
| 9,630,323 B2* | 4/2017 | Kishi | B25J 9/1697 |
| 2002/0045888 A1* | 4/2002 | Ramans | A61B 34/30 |
| | | | 606/1 |
| 2002/0120252 A1* | 8/2002 | Brock | A61B 17/0469 |
| | | | 606/1 |
| 2005/0117207 A1 | 6/2005 | Haisch | |
| 2005/0166413 A1* | 8/2005 | Crampton | B25J 13/088 |
| | | | 33/503 |
| 2006/0274444 A1 | 12/2006 | Haisch | |
| 2010/0168919 A1* | 7/2010 | Okamoto | B25J 9/06 |
| | | | 700/275 |
| 2010/0274078 A1* | 10/2010 | Kim | A61B 1/00149 |
| | | | 600/102 |
| 2012/0143353 A1* | 6/2012 | Kishi | B25J 3/04 |
| | | | 700/3 |
| 2014/0246473 A1* | 9/2014 | Auld | A61B 17/068 |
| | | | 227/175.1 |
| 2016/0135909 A1* | 5/2016 | Ogawa | B25J 9/06 |
| | | | 606/130 |

FOREIGN PATENT DOCUMENTS

| | | |
|---|---|---|
| JP | 10-14938 A | 1/1998 |
| JP | 10-249769 A | 9/1998 |
| JP | 2001-112777 A | 4/2001 |
| JP | 2003-310638 A | 11/2003 |
| JP | 2005-292452 A | 10/2005 |
| JP | 2011-502807 A | 1/2011 |

OTHER PUBLICATIONS

International Search Report dated Oct. 27, 2015 in PCT/JP2015/071009 filed Jul. 23, 2015.
Extended European Search Report dated Feb. 1, 2018 in Patent Application No. 15826949.8, 8 pages.

* cited by examiner

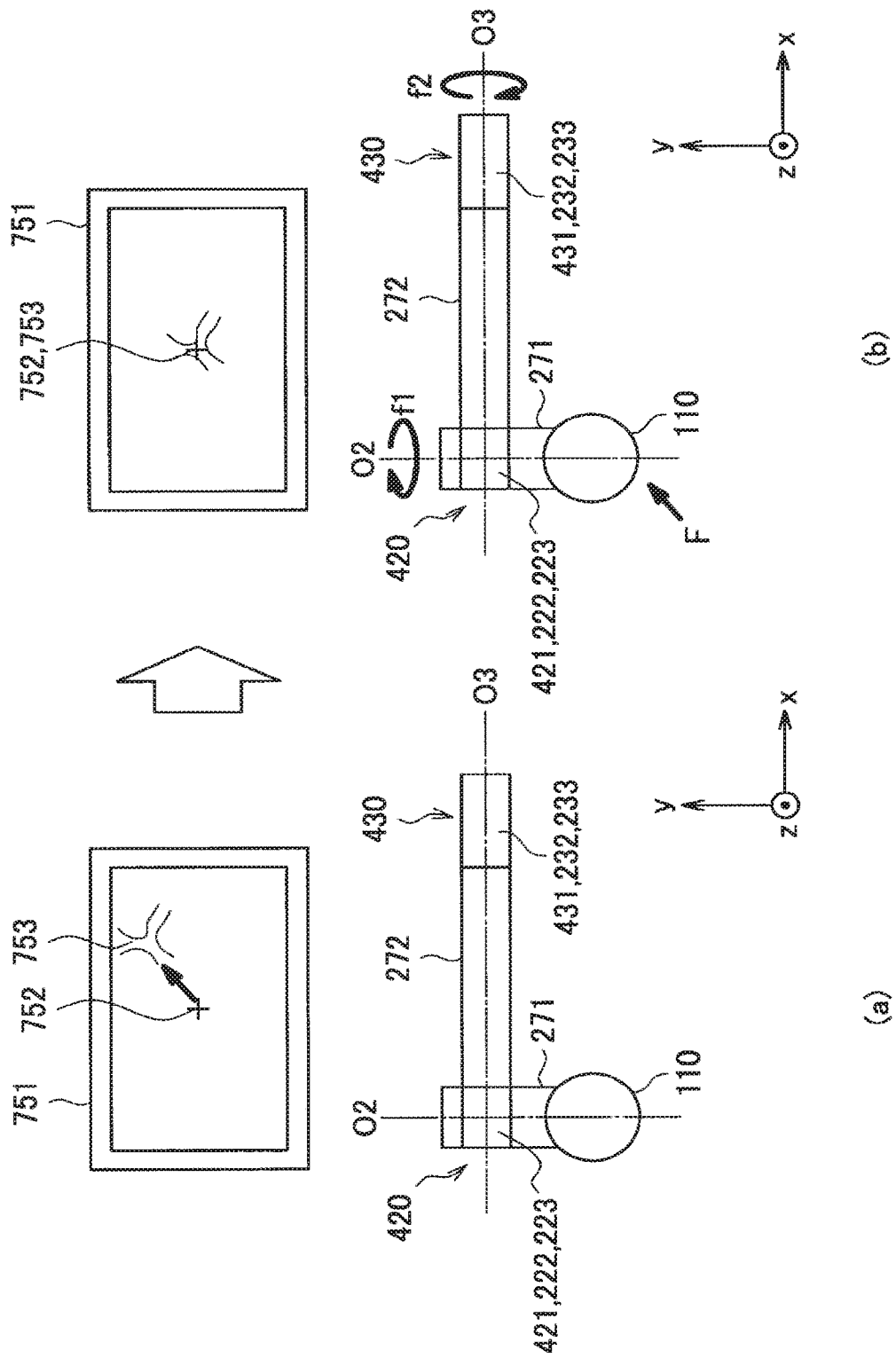

MEDICAL OBSERVATION DEVICE

TECHNICAL FIELD

The present disclosure relates to a medical observation device.

BACKGROUND ART

For surgical operations of cranial neurosurgery, medical microscopes (operating microscopes) have been used to perform operations, enabling tiny operation sites to be enlarged and observed in the past. Since operation sites are very small areas in surgical operations of cranial neurosurgery for example, it is demanded to move and fix positions and attitudes of operating microscopes with high precision. Thus, technologies for holding operating microscopes with balance arms or robot arms have been developed.

Meanwhile, there have been demands in surgical operations for enabling the same operation site to be observed from different angles by tilting-moving an operating microscope with an observation point fixed (in other words, with the observation point positioned on the optical axis of the operating microscope at all times). Such an operation of moving an operating microscope with an observation point fixed is also called a point lock operation or a pivot operation, and observation of an operation site using the point lock operation or the pivot operation is also called point lock observation or pivot observation. Technologies for realizing the point lock operation for balance arms and robot arms which hold operating microscopes have been developed.

For example, Patent Literature 1 discloses a balance arm by which a movable range of an operating microscope is mechanically regulated and the point lock operation is realized by configuring a holding unit (an arm unit) which holds the operating microscope to be combined with a plurality of parallelogrammic link mechanisms. In addition, Patent Literature 2, for example, discloses a robot arm with six degrees of freedom which detects a position and an attitude of a patient based on markers attached to the patient, and is driven to automatically perform predetermined treatment on the patient using a medical treatment instrument connected to a front end thereof. The technology described in Patent Literature 2 has a possibility of realizing the point lock operation by providing a medical microscope, instead of a treatment instrument, and appropriately controlling driving of respective joints of a holding unit through, for example, position control.

CITATION LIST

Patent Literature

Patent Literature 1: JP H8-266555A
Patent Literature 2: JP 2011-502807T

DISCLOSURE OF INVENTION

Technical Problem

However, in order to mechanically regulate movement of the operating microscope in the technology described in Patent Literature 1 mentioned above, the holding unit has a complicated configuration in which the unit includes double balance arms, and thus there is a possibility of the device increasing in size. In addition, in the robot arm having six degrees of freedom as described in Patent Literature 2 mentioned above, the configuration of the holding unit in which joints should be driven becomes larger from the joint at the front end (on the side to which a treatment instrument or the medical microscope is connected) toward the joint on the rear side (the side which corresponds to the base of the holding unit), and thus driving devices (for example, actuators) mounted in the joints are demanded to produce greater outputs when the devices are positioned further rearward. Therefore, the robot arm with six degrees of freedom tends to have joints having a larger structure when they are positioned further rearward, and thus there is a concern of the whole device increasing in size.

In the technologies described in Patent Literature 1 and 2, there are possibilities of configurations of the devices increasing in their sizes as described above. Meanwhile, it is assumed in a surgical operation that point lock observation is performed a plurality of times and an observation point and observation direction at those times can also variously change. Thus, it is desired in point lock observation to move a microscope simply through manual manipulation. Taking the above circumstances into account, there is demand for a technology for realizing a desired operation of a user such as a point lock operation which ensures an excellent manipulation property with a smaller and simpler configuration.

Therefore, the present disclosure proposes a novel and improved medical observation device which ensures an excellent manipulation property with a smaller and simpler configuration.

Solution to Problem

According to the present disclosure, there is provided a medical observation device including: an imaging unit configured to photograph an image of an operation site; a holding unit configured to be connected with the imaging unit and have rotary shafts which are operable with at least six degrees of freedom. Among the rotary shafts, at least two shafts are active shafts whose driving is controlled based on states of the rotary shafts, and at least one shaft is a passive shaft which is rotated according to direct external manipulation accompanying contact.

According to the present disclosure, there is provided a medical observation device including: an imaging unit configured to photograph an image of an operation site; and a holding unit configured to be connected with the imaging unit and have rotary shafts which are operable with at least six degrees of freedom. Among the rotary shafts, at least two shafts, which are a first rotary shaft which is orthogonal to an optical axis of the imaging unit and a second rotary shaft which is orthogonal to the optical axis and the first rotary shaft, are active shafts whose driving is controlled based on states of the rotary shafts, and at least one shaft is a passive shaft which is rotated according to direct external manipulation accompanying contact, and the first and second rotary shafts have encoders configured to detect rotation angles of the first and second rotary shafts, force sensors configured to detect external force loaded at least on the first and second rotary shafts, and actuators configured to drive rotation of the first and second rotary shafts.

According to the present disclosure, at least the two shafts among the rotary shafts provided in the holding unit having at least six degrees of freedom function as active shafts driven based on states of the respective rotary shafts, and at least one shaft functions as a passive shaft which is rotated according to direct manipulation. By appropriately controlling driving of the active shafts in that manner while a simpler configuration with a reduced number of active shafts is employed, a satisfactory manipulation property can be realized in an operator's (user's) desired operation.

Advantageous Effects of Invention

According to the present disclosure described above, an excellent manipulation property can be ensured with a smaller and simpler configuration. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 11 is an illustrative diagram for describing movement of an imaging unit when a modified example in which the imaging unit is moved through force control based on sensing of stress is applied.

MODE(S) FOR CARRYING OUT THE INVENTION

Figure 1:
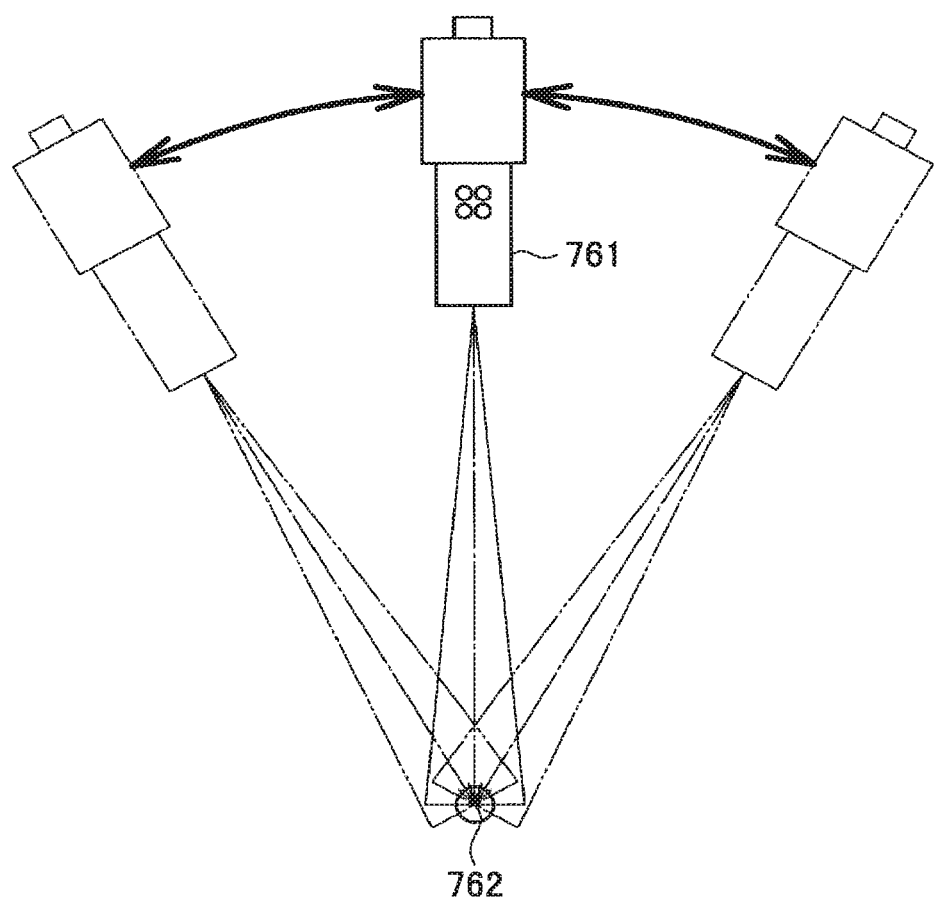
FIG. 1 is an illustrative diagram for describing a movement of a microscope at the time of point lock observation.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.

1. Review of general medical observation devices
2. First Embodiment
2-1. Configuration of device
2-2. Operation in use
2-3. Functional configuration of device
3. Second Embodiment
3-1. Configuration of device
3-2. Operation in use
3-3. Functional configuration of device
4. Third Embodiment
4-1. Configuration of device
4-2. Operation in use
5. Modified examples
5-1. Modified example in which imaging unit has AF function
5-2. Modified example in which imaging unit is moved using force control based on sensing of stress
6. Supplement 1. Review of General Medical Observation Devices Before an exemplary embodiment of the present disclosure is described, the result of review by the present inventors of general medical observation devices will be described, and the reason for conceiving the embodiments to be described below will be described.

As described above, there are cases in surgical operations in cranial neurosurgery, etc., in which, for example, an operation site is photographed using an operating microscope (hereinafter also referred to simply as a microscope) and an operator executes the surgical operation viewing the photographed image. In order to adjust a position and an attitude of the microscope with high precision, a medical observation device which holds the microscope with a balance arm or a robot arm is used. For example, by configuring a holding unit (arm unit) which holds the microscope with a balance arm having a counterweight, the operator can move the microscope, feeling as if it were weightless.

Here, a case in which the microscope is generally held with a holding unit having six degrees of freedom will be considered. Movements of the microscope can be classified into two, which are translational movement and tilting movement. Positions of the microscope change within a plane in translational movement, and attitudes of the microscope (i.e., an observation direction (a direction of its optical axis)) change in tilting movement. Also depending on attitudes of the microscope, translational movement can be realized by, for example, causing 1 to 3 degrees of freedom out of six degrees of freedom to function. By translationally moving the microscope while viewing an image photographed by the microscope (a captured image), the operator can relatively easily perform movement of the microscope such that the center of a visual field moves from an observation point to the next observation point a predetermined distance away therefrom while capturing the former observation point within the visual field.

Meanwhile, during a surgical operation, there is a desire to observe the same operation site from different angles, i.e., a desire to perform point lock observation, for example, to observe a side of a target object such as a blood vessel or to observe a site of a blind area. FIG. 1 schematically shows movement of a microscope at the time of point lock observation. FIG. 1 is an illustrative diagram for describing the movement of the microscope at the time of point lock observation.

As illustrated, when point lock observation is performed, the microscope 761 is moved such that an observation point 762 is positioned on the optical axis of the microscope 761 at all times, i.e., the observation point 762 with respect to the microscope 761 after the movement coincides with the observation point 762 with respect to the microscope 761 before the movement. In order to realize this operation, the microscope 761 needs to perform complicated movement in which translational movement and tilting movement are combined.

A case in which, for example, an operator manually moves the microscope 761 using an existing general balance arm to perform point lock observation will be considered. In this case, since it is hard for the operator to ascertain a precise position and attitude of the microscope 761 to be set after movement in advance, the operator has to execute a combination of manipulation of translational-moving the microscope 761 and manipulation of tilting-moving the microscope 761 while viewing an image captured by the microscope 761, and to search for a desired position and attitude of the microscope 761.

Manipulation to move the microscope 761 itself is not a heavy burden because the operator moves the microscope 761 with less power using the balance arm. However, in a so-called micro surgery performed in a surgical operation in cranial neurosurgery, for example, the operator may perform the surgical operation while viewing an enlargement of a small range having a diameter of about 30 (mm) at a high magnification ratio. Thus, when a position and an attitude of the microscope 761 are changed, the observation point easily goes out of its visual field. Thus, it is hard to say that searching for a position and an attitude of the microscope 761 in which an observation point can be observed from a desired direction while including the observation point in its visual field is simple manipulation. In addition, it is generally assumed that, during a surgical operation, point lock observation is frequently performed while observation points are changed. Thus, enabling the microscope 761 to be moved simply through manual manipulation in point lock observation is desired.

Thus, by studying the configuration of the holding unit and mechanically regulating movement of the microscope to realize the point lock operation with regard to the balance arm described in Patent Literature 1 above, movement of the microscope 761 is possible through relatively simple manipulation during point lock observation. However, since the balance arm described in Patent Literature 1 mechanically regulates movement of the microscope, there is a possibility of the configuration of the holding unit becoming complicated and the device increasing in its size and weight. In addition, control for attitudes of an operating microscope is transmitted by a transmission member such as a wire, and thus due to a mechanical shift between members, for example, a shift of an observation point caused by deterioration of such a wire resulting from aging, there is a possibility of a point lock operation not being realized as intended.

In addition, as described above, Patent Literature 2 discloses as well a technology for the robot arm having six degrees of freedom in which a treatment instrument installed at a front end of the holding unit is automatically moved according to a predetermined program by actively controlling driving of respective joints using driving devices mounted in the respective joints. In the technology described in Patent Literature 2, as the microscope is mounted as a treatment instrument and driving of the respective joints are appropriately controlled through, for example, position control, cumbersome manipulation of an operator is unnecessary, and movement of the microscope corresponding to the point lock operation can be realized. In the configuration in which all the joints include the driving devices, however, the driving devices of the joints disposed in the rear side of the holding unit (the side which corresponds to the base of the holding unit) are demanded to produce an output sufficient for supporting and moving the constituent elements positioned at a further frontward side of the driving devices in the holding unit, and thus there is also a possibility of the device increasing in size.

Here, because there are other devices and many staff members executing or assisting a surgical operation in an operation room, devices used in a surgical operation are demanded to be smaller in general. However, in existing medical observation devices exemplified in Patent Literature 1 or 2 mentioned above, while there is a possibility of movement manipulation of the microscope performed during point lock observation being relatively simple, the devices tend to be larger in size, and thus it is hard to say that a demand for miniaturization of devices is fulfilled at all times.

On the other hand, among robot arms that can actively control driving of each joint in the same way, there is one which can realize the manipulation property close to that of a balance arm by controlling driving of each of joints through force control such that dynamic imbalance in moments of a holding unit is cancelled out. However, joints of such a robot arm are configured with actuators and deceleration mechanisms in most cases, and such a configuration is likely to have difficulty realizing smooth movement and an inferior manipulation property in comparison to a balance arm of which each rotary shaft is configured simply with shaft bearings (bearings).

As a result of reviewing general medical observation devices as described above, the present inventors have acknowledged that there are demands for a technology that can realize a desired operation of users such as the point lock operation in a smaller and simpler configuration while an excellent manipulation property is maintained. After serious discussion about a configuration which satisfies the demands described above, the present inventors have conceived the exemplary embodiments of the present disclosure. Hereinafter, several exemplary embodiments of the present disclosure that the present inventors have conceived will be described in detail.

2. First Embodiment (2-1. Configuration of Device)

Figure 2:
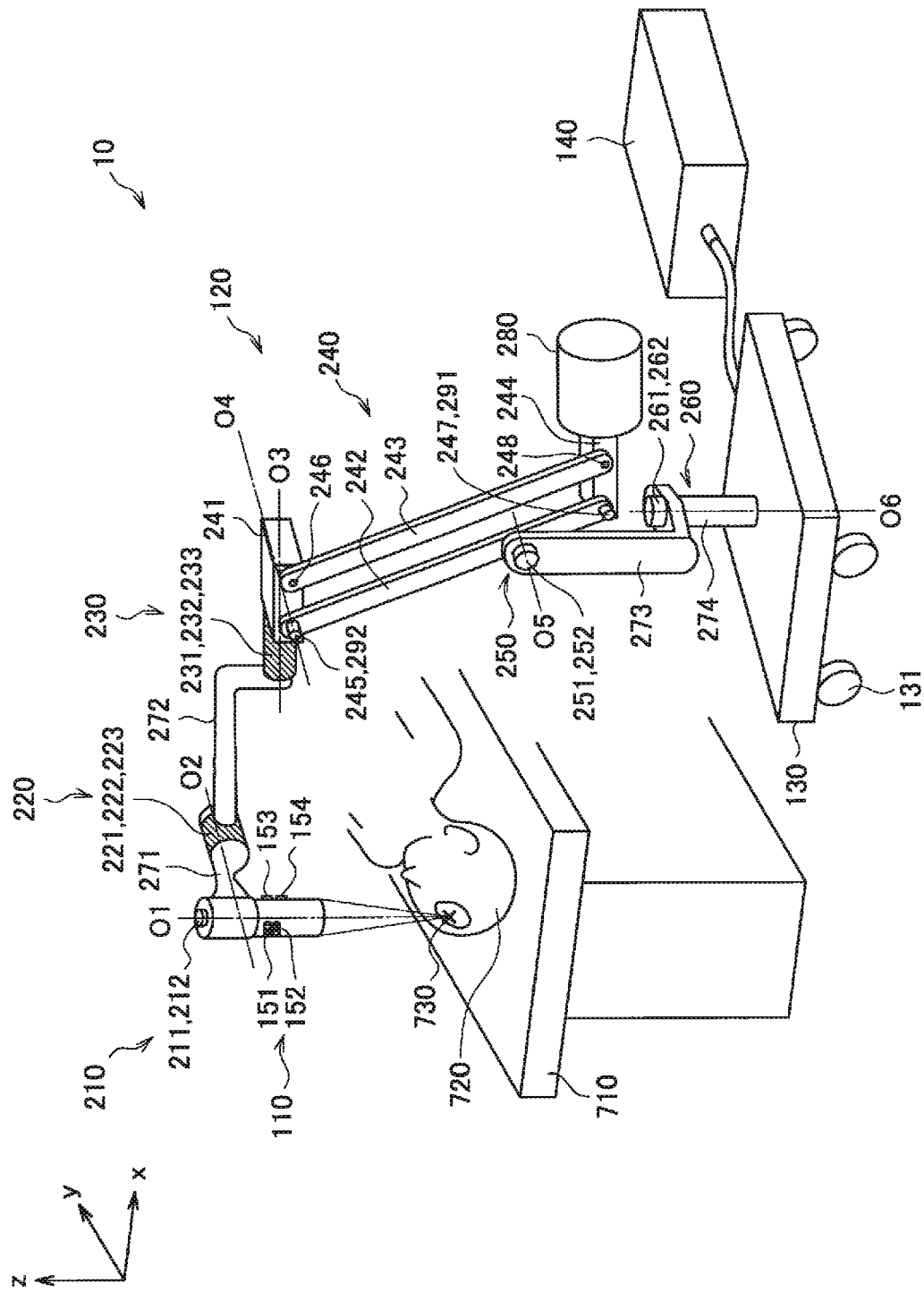
FIG. 2 is a diagram showing an example of a configuration of a medical observation device according to a first embodiment of the present disclosure.
Figure 3:
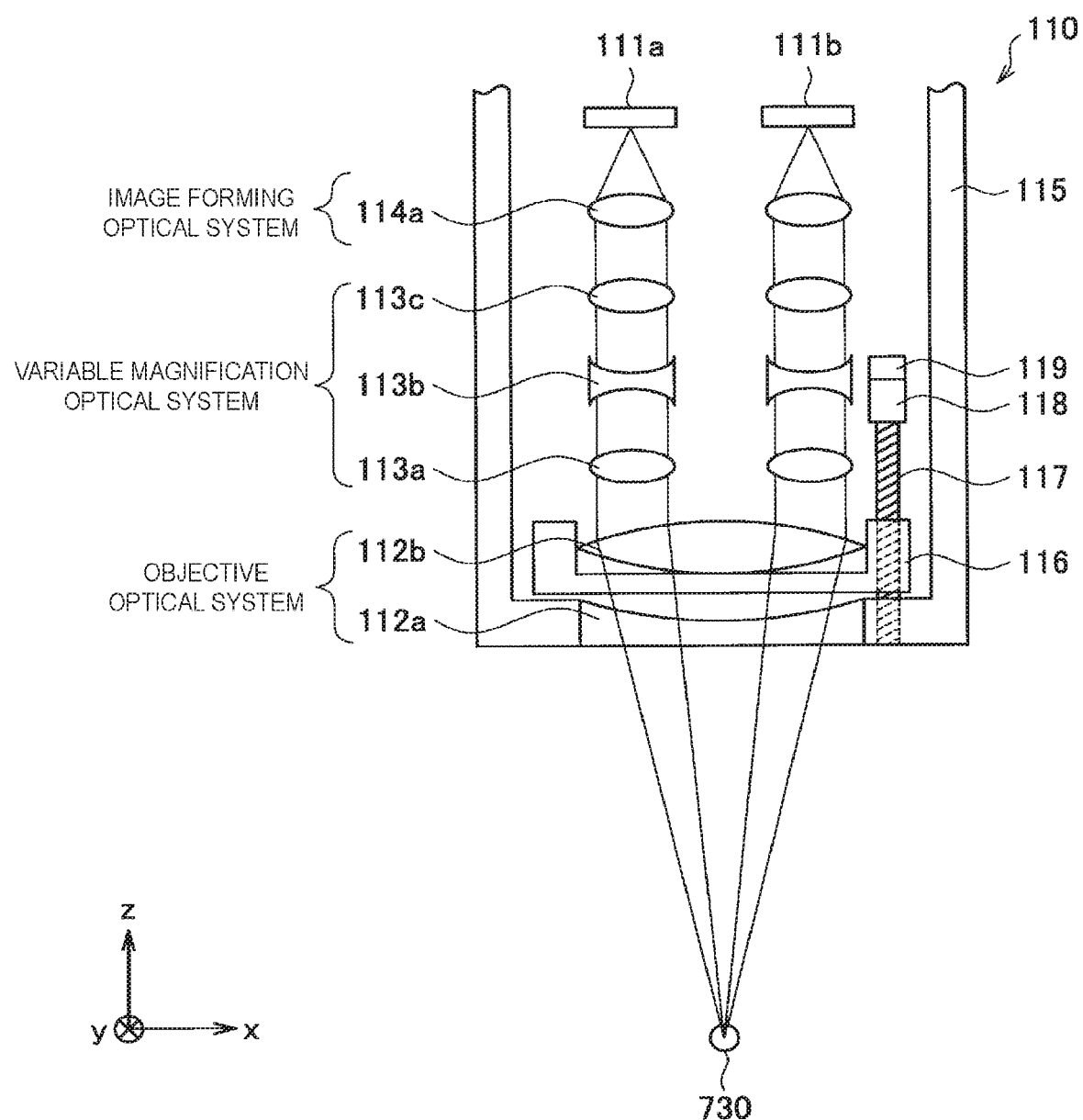
FIG. 3 is a diagram showing an example of a configuration of an imaging unit shown in FIG. 2.
Figure 4:
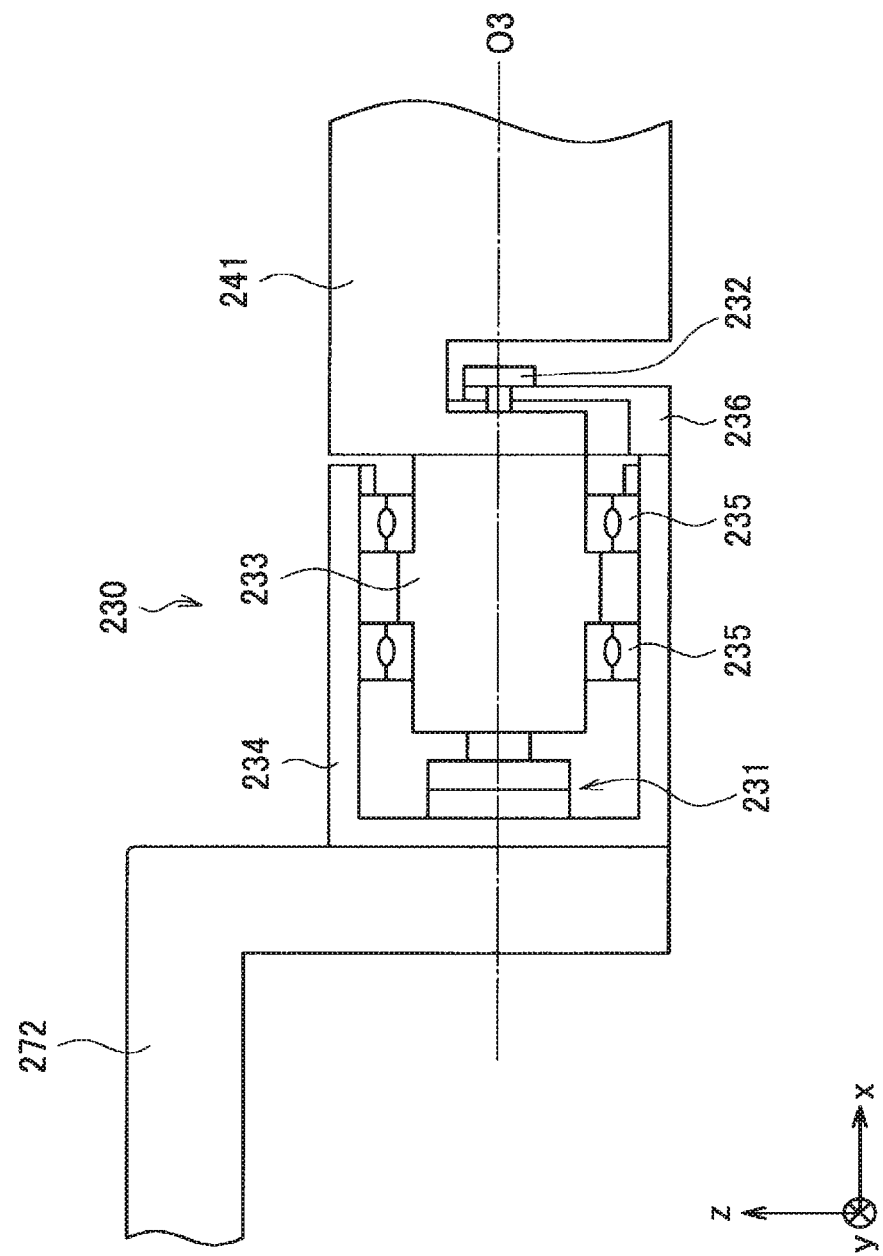
FIG. 4 is a diagram showing an example of a configuration of a rotary axis unit corresponding to an active shaft of a rotary axis unit shown in FIG. 2.

A configuration of a medical observation device according to a first embodiment of the present disclosure will be described with reference to FIGS. 2 to 4. FIG. 2 is a diagram showing an example of the configuration of the medical observation device according to the first embodiment of the present disclosure. FIG. 3 is a diagram showing an example of a configuration of an imaging unit shown in FIG. 2. FIG. 4 is a diagram showing an example of a configuration of a rotary shaft part corresponding to an active shaft of the rotary shaft part shown in FIG. 2. Note that a user who performs various kinds of manipulation of the medical observation device will be hereinafter described as an operator for the sake of convenience. The description, however, does not limit users who use the medical observation device, and various kinds of manipulation of the medical observation device may be executed by all users, such as other members of medical staff.

Referring to FIG. 2, the medical observation device 10 according to the first embodiment includes an imaging unit 110 which photographs an operation site of a patient, a holding unit 120 (an arm unit 120) which holds the imaging unit 110, a base 130 (base 130) which supports the holding unit 120 and the imaging unit 110 with which one end of the holding unit 120 is connected, and a controller 140 which controls operations of the medical observation device 10. FIG. 2 shows a state in which the imaging unit 110 of the medical observation device 10 is photographing an operation site 730 (an observation point 730) of a patient 720 who is lying on an operating table 710.

The base 130 supports the imaging unit 110 and the holding unit 120. The base 130 has a plate shape, and one end of the holding unit 120 is connected to the upper surface of the base. The other end (the front end) of the holding unit 120 extending from the base 130 is connected with the imaging unit 110. A plurality of casters 131 are provided on the lower surface of the base 130, and the medical observation device 10 comes in contact with the floor via the casters 131. The medical observation device 10 is configured to be movable on floors with the casters 131.

Note that, in description below, a vertical direction to the floor on which the medical observation device 10 is installed will be defined as a z axis direction. In addition, two directions orthogonal to the z axis direction will be defined respectively as an x axis direction and a y axis direction. In the illustrated example, the optical axis direction of the imaging unit 110 substantially coincides with the z axis direction.

The controller 140 is configured with, for example, a processor such as a central processing unit (CPU) or a digital signal processor (DSP), a microcomputer in which such a processor is mounted, or the like, and executes arithmetic operation processes according to a predetermined program to control operations of the medical observation device 10. In the first embodiment, for example, the holding unit 120 has a plurality of operation modes (a fixed mode, an all-free mode, and a point lock mode). The controller 140 can switch the operation modes of the holding unit 120 according to manipulation inputs of an operator. Here, the fixed mode is an operation mode in which a position and an attitude of the imaging unit 110 are fixed by regulating rotation of respective rotary shafts provided in the holding unit 120 with brakes. The all-free mode is a state in which respective rotary shafts provided in the holding unit 120 can be rotated freely by releasing the brakes, and an operation mode in which a position and an attitude of the imaging unit 110 can be adjusted according to direct manual manipulation of an operator. Here, the direct manipulation means manipulation of an operator, for example, with his or her hand brought in contact with the imaging unit 110 to move the imaging unit 110. The point lock mode is a mode in which some of the rotary shafts provided in the holding unit 120 act as passive shafts that are rotated according to direct manipulation from an operator, and other rotary shafts act as active shafts whose rotation driving is controlled based on a predetermined condition, and thereby a point lock operation of the imaging unit 110 is executed.

In addition, the controller 140 controls driving of the active shafts in the above-described point lock mode. Specifically, the controller 140 can compute a distance from the imaging unit 110 to the observation point 730 based on information of a focal length of the imaging unit 110. In addition, encoders (encoders 212, 222, 232, 292, 252, and 262 to be described below) which detect rotation angles of the rotary shafts are provided in the respective rotary shafts of the holding unit 120, and the controller 140 can compute a three-dimensional position and attitude of the imaging unit 110 based on detection values of these encoders. The controller 140 controls driving of actuators provided in the active shafts based on the computed distance from the imaging unit 110 to observation point 730 and the three-dimensional position and attitude of the imaging unit 110 so that the observation point 730 with respect to the imaging unit 110 after movement coincides with the observation point 730 with respect to the imaging unit 110 before movement. Accordingly, the imaging unit 110 is moved in the point lock mode to perform the point lock operation.

Note that the functions of the controller 140 will be described again in (2-3. Functional configuration of device) in detail.

The imaging unit 110 is, for example, a microscope, and photographs the operation site of the patient. The imaging unit 110 is configured to be capable of transmitting image information to a display device (not illustrated) such as a display device. The operator observes the operation site and performs various kinds of treatment on the operation site while viewing a captured image photographed by the imaging unit 110 and displayed on the display device.

The imaging unit 110 includes a zoom switch 151 (a zoom SW 151) and a focus switch 152 (a focus SW 152) for adjusting photographing conditions of the imaging unit 110, and an all-free switch 153 (an all-free SW 153) and a point lock switch 154 (a point lock SW 154) for changing the operation mode of the holding unit 120. The operator manipulates the zoom SW 151 and the focus SW 152, and thereby can adjust a magnification ratio and a focal length of the imaging unit 110 respectively. In addition, the operator manipulates the all-free SW 153 and the point lock SW 154 and thereby can switch the operation mode of the holding unit 120 to any of the fixed mode, the all-free mode, and the point lock mode.

Note that these switches may not necessarily be provided in the imaging unit 110. In the first embodiment, a mechanism having functions equivalent to the switches to receive manipulation inputs may be provided in the medical observation device 10, and a specific configuration of the mechanism is not limited. For example, these switches may be provided in other parts of the medical observation device 10. In addition, commands corresponding to these switches may be remotely input to the medical observation device 10 using an input device such as a remote controller.

In addition, although not illustrated in FIG. 2 in order to avoid complexity of the drawing, a grip part that the operator grips can be provided in a partial area of the imaging unit 110. Holding the grip part, the operator can manually perform translational movement and tilting movement of the imaging unit. Note that, as will be described in (2-2. Operation in use) below, the all-free SW 153 and the point lock SW 154 are manipulated while the operator is gripping the grip part in the first embodiment. Thus, it is desirable to decide positions at which the grip part, the all-free SW 153, and the point lock SW 154 are to be disposed, taking their relative positional relation and a manipulation property for the operator into account.

A configuration of the imaging unit 110 will be described with reference to FIG. 3. FIG. 3 shows a cross-sectional diagram of the imaging unit 110 viewed in a plane that passes through the optical axis. Referring to FIG. 3, a pair of image sensors 111a and 111b corresponding to a so-called stereo camera are provided inside a housing 115 of the imaging unit 110. As the image sensors 111a and 111b, for example, any of various known image sensors, for example, charge coupled device (CCD) sensors, complementary metal-oxide semiconductor (CMOS) sensors, or the like may be applied. When information of an image photographed by the image sensors 111a and 111b is transmitted to a display device installed inside the operating room, a captured image of the operation site is displayed on the display device.

A pair of concave lens 112a and convex lens 112b constituting an objective optical system, convex lenses 113a, concave lenses 113b, and convex lenses 113c constituting a variable magnification optical system, and convex lenses 114a constituting an image forming optical system are disposed in the front stage of the image sensors 111a and 111b. In addition, the convex lenses 113a, the concave lenses 113b, and the convex lenses 113c, and the convex lenses 114a are provided in 2 sets corresponding to the respective image sensors 111a and 111b. Light passes through the concave lens 112a and the convex lens 112b constituting the objective optical system, is incident on the imaging unit 110, and forms an image on the image sensors 111a and 111b, through in the order of the convex lenses 113a, the concave lenses 113b and the convex lenses 113e provided corresponding to each of the image sensors 111a and 111b constituting the variable magnification optical system, and the convex lenses 114a constituting the image forming optical system. Note that, although not illustrated in FIG. 3 in order to avoid complexity of the drawing, each of constituent members provided inside the housing 115 of the imaging unit 110 is appropriately supported by various support members with respect to the housing 115.

One of the concave lens 112a and the convex lens 112b constituting the objective optical system, for example, the concave lens 112a disposed on an outside of the housing 115, is fixed to the housing 115, and the other one, for example, the convex lens 112b disposed further inside, is configured to be movable in the z axis direction (the optical axis direction). As shown in FIG. 3, a lead screw 117 for moving a support member 116 which supports the convex lens 112b with respect to the housing 115 and the convex lens 112b in the z axis direction and a motor 118 for rotating the lead screw 117 in the z axis direction as a rotary shaft direction are disposed in the support member 116. When the motor 118 is driven according to a manipulation input to the above-described focus SW 152, a position of the convex lens 112b on the optical axis is moved, and a focal length of the imaging unit 110 is adjusted. In addition, an encoder 119 for detecting the number of rotations of the motor 118 is provided in the motor 118. A detection value of the encoder 119 can be provided to the controller 140 when necessary. Since the detection value of the encoder 119 is a value indicating a position of the convex lens 112b on the optical axis, the controller 140 can compute a focal length and/or a working distance (WD) of the imaging unit 110 based on the detection value of the encoder 119.

Note that, although the case in which a focal length of the imaging unit 110 is adjusted as the concave lens 112a is configured to be fixed and the convex lens 112b to be movable has been described in the above example, the first embodiment is not limited thereto. A relative distance between the concave lens 112a and the convex lens 112b on the optical axis may be used in order to adjust a focal length of the imaging unit 110 as long as the distance is adjustable, and thus either the concave lens 112a or the convex lens 112b or both may be configured to be movable, and a specific configuration thereof is not limited. In addition, a movement mechanism for moving either the concave lens 112a or the convex lens 112b or both is not limited to the above-described example, and any of various known mechanisms may be used.

Some or all of the convex lenses 113a, the concave lenses 113b, and the convex lenses 113c constituting the variable magnification optical system are configured to be movable in the z axis direction. By moving the convex lenses 113a, the concave lenses 113b and/or the convex lenses 113c on the optical axis, a magnification ratio of an image captured by the imaging unit 110 can be adjusted. Note that, although not illustrated in FIG. 3 for the sake of simplicity, a movement mechanism for moving the convex lenses 113a, the concave lenses 113b, and/or the convex lenses 113c in the z axis direction is also provided, like the convex lens 112b. When the movement mechanism is driven according to a manipulation input to the above-described zoom SW 151, positions of the convex lenses 113a, the concave lenses 113b, and/or the convex lenses 113c on the optical axis are moved, and thus a magnification ratio of the imaging unit 110 can be adjusted.

The configuration of the imaging unit 110 has been described above in detail with reference to FIG. 3.

Returning to FIG. 2, description of the configuration of the medical observation device 10 will be continued. The holding unit 120 holds the imaging unit 110, allows the imaging unit 110 to move 3-dimensionally, and helps a position and an attitude of the imaging unit 110 after movement to be fixed. In the illustrated example, the holding unit 120 is configured as a balance arm having six degrees of freedom. The first embodiment, however, is not limited thereto. The holding unit 120 may be configured to have at least six degrees of freedom, and to have so-called redundant degrees of freedom, like seven or more degrees of freedom. In addition, the holding unit 120 may not necessarily be configured as a balance arm. Even when the holding unit 120 is not configured as a balance arm in the first embodiment, the point lock operation can be executed. However, if the holding unit 120 is configured as a balance arm and the imaging unit 110 and the holding unit 120 are configured to establish balancing of moments as a whole, the imaging unit 110 can be moved with lighter external force and the manipulation property for the operator can be further enhanced.

6-axial rotary shafts which realize six degrees of freedom are provided in the holding unit 120. For the sake of convenience of description, members constituting a rotary shaft will be collectively referred to as a rotary shaft part. The rotary shaft part can be constituted by, for example, a shaft bearing (a bearing), a shaft which is turnably inserted into the shaft bearing, a sensor member which detects a state (for example, a rotation angle, etc.) of the rotary shaft, a brake which regulates rotation of the rotary shaft, and the like. A configuration of a rotary shaft part may be different according to whether its rotary shaft is an active shaft or a passive shaft to be described below. In addition, with regard to a parallelogrammic link mechanism 240 to be described below, because the parallelogrammic link mechanism 240 can constitute a rotary shaft, the parallelogrammic link mechanism 240 can be regarded as a rotary shaft part.

The holding unit 120 is constituted by the rotary shaft parts 210, 220, 230, 250, and 260 each corresponding to a rotary shaft (hereinafter abbreviated to rotary shaft parts 210 to 260) and the parallelogrammic link mechanism 240, arms 271 to 274 which connect the rotary shaft parts 210 to 260 and the parallelogrammic link mechanism 240, and a counterweight 280 for establishing a balance of moments of the whole imaging unit 110 and holding unit 120. Hereinbelow, description will be provided with regard to rotary shafts named O1 shaft to O6 shaft, respectively. The rotary shaft that is closest to the imaging unit 110 is an O1 shaft, and the rotary shaft that is closest to the base 130 is an O6 shaft.

The rotary shaft part 210 is provided to be capable of turning the imaging unit 110, using a rotary shaft that substantially coincides with the optical axis of the imaging unit 110 (the O1 shaft) as a rotary shaft direction. As the rotary shaft part 210 turns imaging unit 110 around the O1 shaft, a direction of a captured image of the imaging unit 110 is adjusted.

A brake 211 and the encoder 212 are mounted in the rotary shaft part 210. The encoder 212 detects a rotation angle of the O1 shaft. The brake 211 is driven by manipulation on the above-described all-free SW 153 and point lock SW 154 to regulate rotation around the O1 shaft when necessary. While the brake 211 is functioning, it is possible to prevent rotation of the imaging unit 110 around the O1 shaft from occurring, for example, even when an operator applies external force manually. Like the rotary shaft pan 210, a rotary shaft part in which an active driving mechanism such as an actuator is not provided can constitute a rotary shaft that rotates according to direct manual manipulation of the operator while no brake is functioning (for example, in the above-described all-free mode or point lock mode). In the present specification, a rotary shaft which rotates according to such a direct manual manipulation will also be referred to as a passive shaft.

The rotary shaft part 210 is connected with an end of the arm 271 extending in a direction substantially orthogonal to the O1 shaft. In addition, the rotary shaft part 220 configured to be capable of turning the arm 271 using the extension direction of the arm 271 as a rotary shaft direction (the O2 shaft direction) is provided at the other end of the arm 271. The O2 shaft is disposed substantially perpendicular to the O1 shaft, and is provided as a rotary shaft substantially parallel to the y axis in the example shown in FIG. 2. As the rotary shaft part 220 turns the imaging unit 110 and the arm 271 using the O2 shaft as a rotary shaft, a position of the imaging unit 110 in the x axis direction is adjusted.

The rotary shaft part 220 includes a brake 221, an encoder 222, and an actuator 223. Since functions of the brake 221 and the encoder 222 are similar to those of the brake 211 and the encoder 212 provided in the rotary shaft part 210, detailed description thereof will be omitted. The actuator 223 is configured with, for example, an electric motor such as a servo motor, is driven under control from the controller 140 in the above-described point lock mode, and causes the rotary shaft part 220 to rotate by a given angle. A rotation angle of the rotary shaft part 220 is set to a value necessary for moving the imaging unit 110 so that the observation point 730 is not changed before and after the movement of the imaging unit 110 by the controller 140 based on a rotation angle of each of the rotary shafts O1 to O6. Like the rotary shaft part 220, a rotary shaft part in which an active driving mechanism such as an actuator is provided can constitute a rotary shaft that actively rotates as driving of the actuator is controlled in, for example, the point lock mode. In the present specification, a rotary shaft whose driving of rotation is actively controlled by a driving mechanism will also be referred to as an active shaft. Note that, in FIG. 2, the rotary shaft parts 220 and 230 which correspond to active shafts are illustrated with hatching in order to be distinguished from other rotary shaft parts.

An end of an arm 272 extending in a direction substantially perpendicular to the O1 shaft and the O2 shaft is connected with the rotary shaft part 220. In addition, the rotary shaft part 230 configured to be capable of turning the arm 272 using the extension direction of the arm 272 as a rotary shaft direction (the O3 shaft direction) is provided at the other end of the arm 272. The O3 shaft is disposed to be substantially perpendicular to the O1 shaft and the O2 shaft, and is provided as a rotary shaft substantially parallel to the x axis in the example shown in FIG. 2. As the rotary shaft part 230 turns the imaging unit 110, the arm 271, and the arm 272 using the O3 shaft as a rotation axis, a position of the imaging unit 110 in the y axis direction is adjusted. The rotary shaft part 230 has a brake 231, an encoder 232, and an actuator 233, like the rotary shaft part 220. As described above, the O3 shaft that is a rotary shaft corresponding to the rotary shaft part 230 acts as an active shaft.

In the first embodiment, the holding unit 120 is configured such that at least two shafts among the rotary shafts of the O1 shaft to the O6 shaft function as active shafts, and at least one shaft functions as a passive shaft. In the example shown in FIG. 2, the O2 shaft and the O3 shaft which correspond to the rotary shaft parts 220 and 230 function as active shafts, and the other O1 shaft, O4 shaft, O5 shaft, and O6 shaft corresponding to the rotary shaft parts 210, 250, 260, and the parallelogrammic link mechanism 240 function as passive shafts. As described above, the rotary shaft parts 220 and 230 can control rotation using the x axis and y axis, which are two axes substantially perpendicular to the optical axis of the imaging unit 110, as rotation axes. Thus, among the O1 shaft to the O6 shaft, the O2 shaft and the O3 shaft can be said to be two shafts which can decide a tilt of the imaging unit 110, i.e., the optical axis direction of the imaging unit 110. If rotation around the two shafts substantially perpendicular to the optical axis of the imaging unit 110 can be controlled, the imaging unit 110 can be set to face an arbitrary direction, regardless of a position of the imaging unit 110. Thus, by configuring the holding unit 120 such that the O2 shaft and the O3 shaft function as active shafts and appropriately controlling rotation around the O2 shaft and the O3 shaft based on detection values of rotation angles of the O1 shaft to the O6 shaft, movement of the imaging unit 110 can be controlled to realize the point lock operation.

Here, a configuration of the rotary shaft parts 210 to 260 will be described with reference to FIG. 4, exemplifying the rotary shaft part 230. FIG. 4 shows a cross-sectional diagram of the rotary shaft part 230 viewed in a plane that passes through a rotary shaft (the O3 shaft).

Referring to FIG. 4, the actuator 233 is provided inside a housing 234 of the rotary shaft part 230 such that its rotary shaft (an output shaft) is parallel with the O3 shaft. Shaft bearings 235 are disposed between a side of the actuator 233 and an inner wall of the housing 234, and the actuator 233 is configured to be turnable with respect to the housing 234 when the brake 231 to be described below is released.

The output shaft of the actuator 233 is connected to an inner wall of the housing 234 via the brake 231 in the O3 shaft direction. In this manner, the housing 234 functions as a rotation body which rotates according to driving of the actuator 233. The arm 272 is connected to an outer wall of a wall surface of the housing 234 in the O3 shaft direction, and the arm 272 turns along with the housing 234 according to driving of the actuator 233. Note that the brake 231 can be configured as, for example, a mechanical clutch mechanism. When the brake 231 is caused to function, the clutch mechanism releases a mechanical connection between the output shaft of the actuator 233 and the inner wall of the housing 234, and thereby driving of the actuator 233 is not transmitted to the housing 234 which is a rotation body. On the other hand, when the brake 231 is released, the clutch mechanism mechanically connects the output shaft of the actuator 233 and the inner wall of the housing 234, and thus the housing 234 is not rotated by external force, but driving of the actuator 233 enables the housing 234 to rotate. This configuration of the brake 231, however, is not limited thereto, and as the brake 231, another brake mechanism such as an electromagnetic brake which electrically regulates rotation of the housing 234 may be used.

An arm 241 constituting the parallelogrammic link mechanism 240 to be described below is connected with the end of the actuator 233 on the opposite side to the output shaft via, for example, a shaft bearing that is not illustrated. In other words, the actuator 233 is turnably connected with the arm 241. Accordingly, the arm 272 is turnably connected to the arm 241 via the rotary shaft part 230.

In addition, the encoder 232 is connected with the rotary shaft of the actuator 233 on the side to which the arm 241 is connected via a support member 236. The encoder 232 detects the number of rotations and/or a rotation angle of the actuator 233. A detection value of the encoder 232 is provided to the controller 140. The controller 140 can compute a rotation angle of the arm 241, for example, with respect to a reference position on the O3 shaft based on the detection value of the encoder 232.

The configuration of the rotary shaft part 230 has been described above with reference to FIG. 4. Note that, although the configuration of the rotary shaft part 230 has been described above as an example for the rotary shaft parts 210 to 260, the rotary shaft part 220 which corresponds to an active shaft like the rotary shaft part 230, for example, may have a configuration similar to that shown in FIG. 4. In addition, the rotary shaft parts 210, 250, and 260 which correspond to passive shafts may have a configuration similar to that in which the actuator 233 is removed from the configuration shown in FIG. 4. However, since the actuator 233 is not provided in the rotary shaft parts 210, 250, and 260, it is not possible to use the brake 231 configured as the mechanical clutch mechanism described above, and thus, any of various mechanisms which can satisfactorily stop rotational motions of the rotary shaft parts 210, 250, and 260 can be appropriately used as the brake mechanism. For example, an electromagnetic brake may be used as the brake mechanism of the rotary shaft parts 210, 250, and 260.

Returning to FIG. 2, description of the configuration of the holding unit 120 will be continued. The parallelogrammic link mechanism 240 is connected to the end of the rotary shaft part 230 in the direction in which the arm 272 is not connected. The parallelogrammic link mechanism 240 is constituted by four arms 241, 242, 243, and 244 disposed in a parallelogrammic shape and shaft bearings 245, 246, 247, and 248 each provided at positions corresponding to substantially the vertexes of the parallelogram.

Specifically, an end of the arm 241 extending in a direction substantially parallel with the O3 shaft is connected with the rotary shaft part 230. In other words, the arm 272 and the arm 241 are disposed serving as arms extending in substantially the same direction. The shaft bearing 245 is provided at an end of the arm 241, and the shaft bearing 246 is provided at the other end. Ends of the arms 242 and 243 are connected with the shaft bearings 245 and 246 respectively so that the arms can turn around rotary shafts (the O4 shaft) penetrating the shaft bearings 245 and 246 and are substantially parallel with each other.

Furthermore, the shaft bearings 247 and 248 are respectively provided at the other ends of the arms 242 and 243. The arm 244 joins these shaft bearings 247 and 248 to be turnable around rotary shafts (the O4 shaft) penetrating the shaft bearings 247 and 248 and to be substantially parallel with the arm 241. As described above, the parallelogrammic link mechanism 240 is constituted by these four arms 241 to 244 and the four shaft bearings 245 to 248.

Here, the arm 244 is formed to be longer than the arm 241, and one end thereof extends outside of the parallelogrammic link mechanism 240. In addition, it is preferable for the respective arms 242 and 243 to be formed to be longer than a gap between the shaft bearings 247 and 248 of the arm 244. That is, it is preferable for the arms 242 and 243 to be formed to be longer than the arm 241.

In the first embodiment, the O4 shaft that is a rotary shaft which corresponds to the parallelogrammic link mechanism 240 functions as a passive shaft. Thus, like the rotary shaft parts 210, 250, and 260 that function as passive shafts, a brake 291 and an encoder 292 are provided in the parallelogrammic link mechanism 240. In the example shown in FIG. 2, the brake 291 for regulating rotation of the parallelogrammic link mechanism 240 around the O4 shaft is provided in the shaft bearing 247. In addition, the encoder 292 for detecting a rotation angle of the parallelogrammic link mechanism 240 around the O4 shaft is provided in the shaft bearing 245 of the parallelogrammic link mechanism 240. Disposition positions of the brake 291 and the encoder 292, however, are not limited thereto, and they may be provided in any of the four shaft bearings 245 to 248 of the parallelogrammic link mechanism 240.

The rotary shaft part 250 which turnably supports the parallelogrammic link mechanism 240 in a direction perpendicular to the extension direction of the arm 242 set as a rotary shaft direction (the direction of the O5 shaft) is provided at a portion a predetermined distance away from the end of the arm 242 at which the shaft bearing 247 is provided. The O5 shaft is a rotary shaft substantially parallel with the O4 shaft, and is provided as a rotary shaft substantially parallel with the y axis in the example shown in FIG. 2. A brake 251 which regulates rotation around the O5 shaft and the encoder 252 which detects a rotation angle with respect to the O5 shaft are mounted in the rotary shaft part 250. An end of the arm 273 stretching in the z axis direction is connected with the rotary shaft part 250, and the parallelogrammic link mechanism 240 is configured to be turnable with respect to the arm 273 via the rotary shaft part 250.

The arm 273 has a substantially L shape, and the opposite side thereof with respect to the side on which the rotary shaft part 250 is provided is bent to be substantially parallel with the floor. The rotary shaft part 260 which can turn the arm 273 around a rotary shaft (the O6 shaft) orthogonal to the O5 shaft is provided on a surface of the arm 273 that is substantially parallel with the floor. In the example shown in FIG. 2, the O6 shaft is provided as a rotary shaft substantially parallel with the z axis. A brake 261 which regulates rotation around the O6 shaft and the encoder which detects a rotation angle with respect to the O6 shaft are mounted in the rotary shaft part 260. An end of the arm 274 extending in the vertical direction is inserted into the rotary shaft part 260, and the other end of the arm 274 is connected with the base 130.

Here, the counterweight 280 (counterbalance 280) is integrally installed at the end of the arm 244 projecting further outward than the shaft bearing 248 that is positioned diagonally opposite to the shaft bearing 245 provided at the side of the parallelogrammic link mechanism 240 at which the rotary shaft part 230 is connected. The mass and disposition position of the counterweight 280 are adjusted so that rotation moments generated around the O4 shaft and rotation moments generated around the O5 shaft can be offset by the mass of the respective constituent members (i.e., the imaging unit 110, the rotary shaft parts 210, 220, and 230, and the arms 271 and 272) that are disposed on a further forward side of the parallelogrammic link mechanism 240. Note that the counterweight 280 may be detachable. When, for example, counterweights 280 of several types having different masses are provided and the constituent elements disposed at the further front end side than the parallelogrammic link mechanism 240 are changed, a suitable counterweight 280 which can offset rotation moments may be selected according to the change.

In addition, a disposition position of the rotary shaft part 250 corresponding to the O5 shaft is adjusted so that the centers of mass of the respective constituent elements (i.e., the imaging unit 110, the rotary shaft parts 210, 220, and 230, the arms 271 and 272, and the parallelogrammic link mechanism 240) disposed at the further front end side than the rotary shaft part 250 are positioned on the O5 shaft. Furthermore, a disposition position of the rotary shaft part 260 corresponding to the O6 shaft is adjusted so that the centers of mass of the respective constituent elements (i.e., the imaging unit 110, the rotary shaft parts 210, 220, 230, and 250, the arms 271, 272, and 273, and the parallelogrammic link mechanism 240) disposed at the further front end side than the rotary shaft part 260 are positioned on the O6 shaft. By configuring the counterweight 280 and the rotary shaft parts 250 and 260 as described above, when the operator attempts to manually move the imaging unit 110, he or she can move the imaging unit 110 with light force feeling as if it were weightless. Thus, a manipulation property for the user can be enhanced.

The configuration of the holding unit 120 has been described above. As described above, the brakes 211, 221, 231, 291, 251, and 261 (hereinafter abbreviated to the brakes 211 to 261) which regulate rotation of the rotary shafts are provided in the respective rotary shafts of the holding unit 120. As the brakes 211 to 261 are controlled according to control from the controller 140, the operation mode of the holding unit 120 may be switched. Note that the rotary shaft parts 220 and 230 which are active shafts may not necessarily have the brakes 221 and 231. When the brakes 221 and 231 are not provided, rotation of the rotary shaft parts 220 and 230 can be fixed by controlling driving of the actuators 223 and 233 such that a sufficient torque for maintaining positions of the rotary shaft parts 220 and 230 (rotation angles) as they are is generated. In this manner, in the first embodiment, a mechanical brake mechanism may not be provided in the active shafts, and the brake function may be realized by driving the actuators.

In addition, the encoders 212, 222, 232, 292, 252, and 262 (hereinafter abbreviated as the encoders 212 to 262) which detect rotation angles of the rotary shafts are provided in the respective rotation shafts of the holding unit 120. Furthermore, the actuators 223 and 233 are provided in the rotary shaft parts 220 and 230 which correspond to active shafts. Detection values of the encoders 212 to 262 are provided to the controller 140 at a predetermined interval when necessary, and the controller 140 can monitor rotation angles of the respective rotary shafts at all times. Based on the rotation angles of the respective rotary shafts, the controller 140 can compute current states of the imaging unit 110 and the holding unit 120, i.e., positions and attitudes of the imaging unit 110 and the holding unit 120. In the point lock mode, the controller 140 controls driving of the actuators 223 and 233 of the rotary shaft parts 220 and 230 based on the computed positions and attitudes of the imaging unit 110 and the holding unit 120 such that the observation point 730 with respect to the imaging unit 110 after movement coincides with the observation point 730 with respect to the imaging unit 110 before movement.

The configuration of the medical observation device 10 according to the first embodiment has been described above with reference to FIGS. 2 to 4. As described above, according to the first embodiment, the point lock operation is realized by causing the two shafts of the O2 shaft and the O3 shaft to function as active shafts, without actively controlling all the rotary shafts. Therefore, the point lock operation can be executed with a smaller and simpler configuration than, for example, the balance arm having a complicated configuration of the holding unit and the robot arm in which driving devices are provided in all rotary shafts described in Patent Literature 1 and 2 above.

In addition, the holding unit 120 according to the first embodiment can be configured as a balance arm. Thus, even when the operator moves the imaging unit 110 in the point lock operation, he or she can easily move the imaging unit with light force. In this way, a satisfactory manipulation property can be secured with the smaller and simpler configuration according to the first embodiment.

In addition, no active control is performed over a distance between the observation point and the imaging unit 110 in the point lock mode in the first embodiment. That is, in the point lock operation, the imaging unit 110 is moved on a hemisphere having the observation point as its center, facing the observation point, but at this time, no regulation is imposed on the movement of the imaging unit 110 in the diameter direction of the sphere. Thus, a distance between the observation point and the imaging unit 110 can be freely changed during the point lock operation if necessary, and thus convenience of the operator can be improved.

Note that, although illustration and description are omitted above, the medical observation device 10 may further include other constituent elements that a general existing medical observation device can include. For example, the medical observation device 10 can include constituent elements such as an input unit which can input various kinds of information including information to be used in a surgical operation and information necessary for control over driving of the medical observation device 10 to the medical observation device 10, an output unit which can visually and auditorily present various kinds of information to the operator, a communication unit which transmits and receives various kinds of information to and from external apparatuses, a storage unit which stores various kinds of information, and a recording unit which writes various kinds of information in a removable recording medium or reads the information from the removable recording medium.

(2-2. Operation in Use)

Next, an operation in use of the medical observation device 10 according to the first embodiment will be described. First, as preparation before use (before a surgical operation), the whole medical observation device 10 is moved close to the operating table 710 using the casters 131.

When the surgical operation is started, first, an operator presses the all-free SW 153 holding the grip part of the imaging unit 110. The operation mode of the holding unit 120 of the medical observation device 10 is configured to be, for example, the fixed mode when neither the all-free SW 153 nor the point lock SW 154 is pressed, and the all-free mode and the point lock mode when the all-free SW 153 and the point lock SW 154 are pressed respectively. When the all-free SW 153 is pressed, the brakes 211 to 261 of the respective rotary shaft parts 210 to 260 and the parallelogrammic link mechanism 240 are released, and thus the operator can freely move the imaging unit 110 through direct manual manipulation. In this manner, in the all-free mode, all the rotary shafts act as if they were passive shafts.

The operator moves the imaging unit 110 with the all-free SW 153 pressed while viewing an image captured by the imaging unit 110 displayed on, for example, a display device such that an operation site is positioned within the visual field of the imaging unit 110. As described in (2-1. Configuration of device) above, the medical observation device 10 is a balance arm, and thus the operator can easily move the imaging unit 110 with light force. If the imaging unit 110 has been moved to a proper position, for example, a position at which the operation site (observation point) is set at the center of the visual field, the operator then releases the all-free SW 153. Accordingly, the brakes 211 to 261 of the respective rotary shaft parts 210 to 260 and the parallelogrammic link mechanism 240 function, and the operation mode of the holding unit 120 transitions to the fixed mode.

In this state, the operator manipulates the zoom SW 151 and the focus SW 152 to appropriately adjust a magnification ratio and a focal length of the imaging unit 110. Viewing an image captured after the adjustment, the operator performs various kinds of treatment on the operation site.

When the operator wants to perform the point lock operation, i.e., wants to observe the observation point from different direction with the observation point fixed, he or she presses the point lock SW 154. While the point lock SW 154 is being pressed, the brakes 211, 291, 251, and 261 of the rotary shaft parts 210, 250, and 260 and the parallelogrammic link mechanism 240 which correspond to the O1 shaft, the O4 shaft, the O5 shaft, and the O6 shaft that are passive shafts are released. In addition, the state in which the brakes 211 and 231 of the rotary shaft parts 220 and 230 which correspond to the O2 shaft and the O3 shaft that are active shafts are functioning is maintained without change. Accordingly, rotation around the O1 shaft, the O4 shaft, the O5 shaft, and the O6 shaft becomes possible through manual manipulation directly performed by the operator.

On the other hand, the controller 140 shown in FIG. 2 monitors a detection value of the encoder 119 provided for the objective optical system of the imaging unit 110 shown in FIG. 3 (i.e., a value indicating a position of the convex lens 112*b* on the optical axis), and detection values of the encoders 212 to 262 of the rotary shaft parts 210 to 260 and the parallelogrammic link mechanism 240 (i.e., values of rotation angles of the O1 shaft to the O6 shaft) at all times. Based on the detection values of the encoders 119 and 212 to 262, the controller 140 calculates a three-dimensional position of the observation point with respect to the holding unit 120 at the time point at which the point lock SW 154 was pressed. In addition, when the operator attempts to move the imaging unit 110 with the point lock SW 154 pressed, the controller 140 computes positions and attitudes of the imaging unit 110 and the holding unit 120 after the movement based on the detection values of the encoders 212 to 262 of the rotary shaft parts 210 to 260 and the parallelogrammic link mechanism 240 when necessary. As described above, the controller 140 can detect a three-dimensional position of the observation point with respect to the holding unit 120 at the time point at which the point lock SW 154 was pressed at all times when positions and attitudes of the imaging unit 110 and the holding unit 120 are changed. Based on the information, the controller 140 executes the point lock operation in which the observation point at the time point at which the point lock SW 154 is pressed is set as a reference point (a point-lock point). To be specific, based on three-dimensional position information of the detected point-lock point with respect to the holding unit 120, the controller 140 can control driving of the actuators 223 and 233 of the rotary shaft parts 220 and 230 such that the optical axis of the imaging unit 110 passes through the observation point at all times before and after the change of the position of the imaging unit 110.

When the operator moves the imaging unit 110 while the point lock SW 154 is being pressed, i.e., during the point lock operation, as described above, rotation around the O1 shaft, the O4 shaft, the O5 shaft, and the O6 shaft which are passive shafts occurs through the manipulation of the operator, and thus rotation around the optical axis and three-dimensional translational movement of the imaging unit 110 is performed. On the other hand, a relative positional relation between the observation point and the imaging unit 110 and the holding unit 120 after the movement is computed from movement amounts (rotation amounts) of these passive shafts, and based on the computed information, rotation around the O2 shaft and the O3 shaft which are active shafts, i.e., tilting movement of the imaging unit 110, is controlled such that the optical axis of the imaging unit 110 passes through the same observation point before and after the movement. Accordingly, even if the operator moves the position of the imaging unit 110 loosely, the imaging unit 110 is tilted facing the observation point at all times, without losing sight of the observation point.

When the imaging unit 110 is moved to a desired position, the operator releases the point lock SW 154 to cause the operation mode of the holding unit 120 to transition to the fixed mode, and thereby the position of the imaging unit 110 is fixed. Observing the operation site from different directions, the operator can perform proper treatment on the operation site.

The operation in use of the medical observation device 10 according to the first embodiment has been described above. Since the operator moves the imaging unit 110 to adjust the visual field with the all-free SW 153 pressed, it is desirable for the all-free SW 153 to be disposed at a position at which it can be easily pressed while the operator is holding the grip part of the imaging unit 110. On the other hand, when the point lock operation is performed, the operator may perform manipulation of moving the position of the imaging unit 110 loosely in his or her own sense, without having to perform fine manipulation such as adjustment of the visual field, and thus the point lock SW 154 may be disposed at any site on the imaging unit 110 in a range in which a finger of the operator reaches, without taking a positional relation with respect to the grip part into particular account.

(2-3. Functional Configuration of Device)

Figure 5:
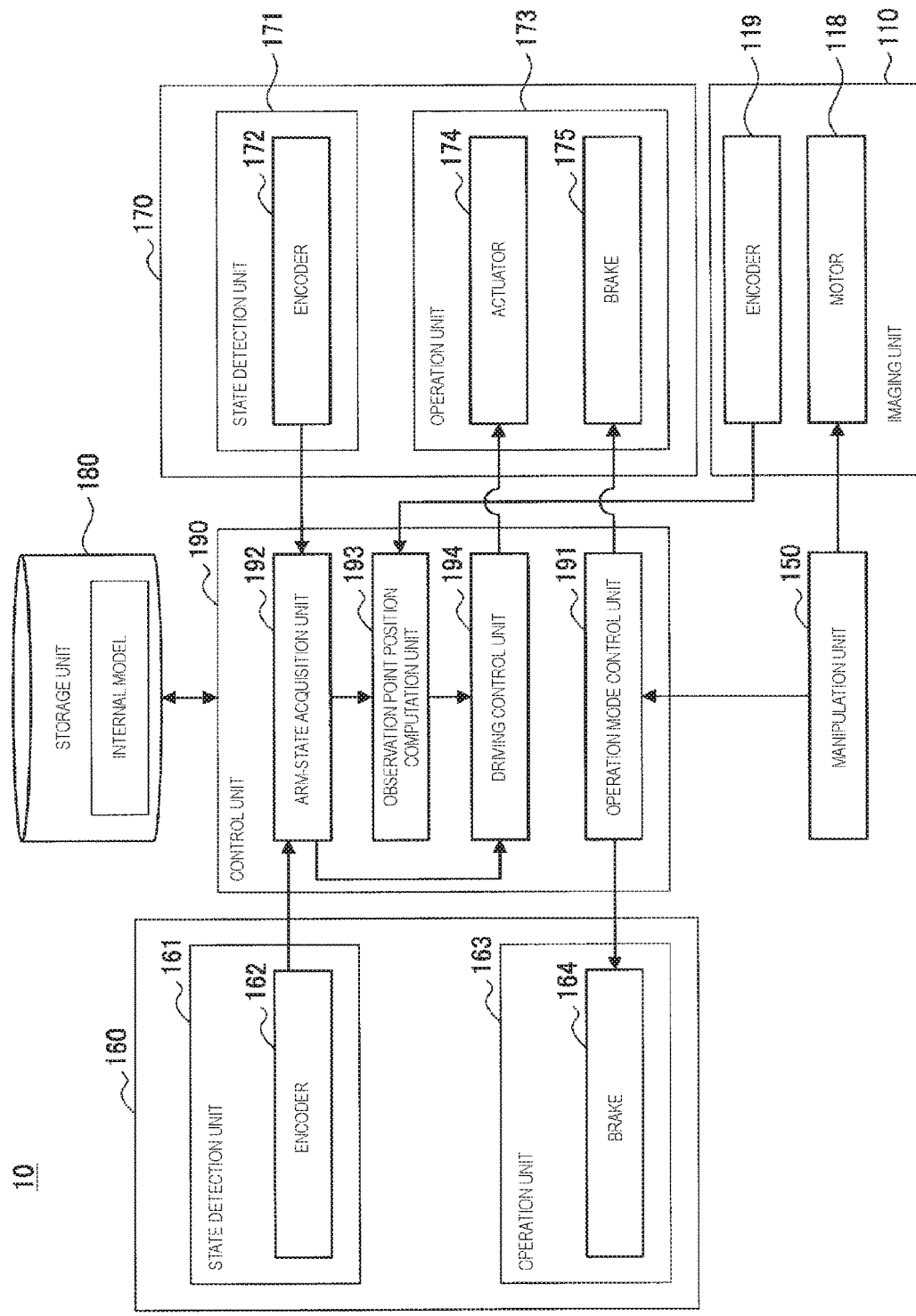
FIG. 5 is a functional block diagram showing an example of a functional configuration of the medical observation device according to the first embodiment.

Next, a functional configuration of the medical observation device 10 according to the first embodiment described with reference to FIG. 2 will be described with reference to FIG. 5. FIG. 5 is a functional block diagram showing an example of the functional configuration of the medical observation device 10 according to the first embodiment.

Referring to FIG. 5, the medical observation device 10 includes an imaging unit 110, a manipulation unit 150, rotary shaft parts 160 and 170, a storage unit 180, and a control unit 190.

The imaging unit 110 is, for example, a microscope, and photographs an operation site of a patient. The imaging unit 110 corresponds to the imaging unit 110 shown in FIGS. 2 and 3. As described with reference to FIG. 3, the imaging unit 110 has the motor 118 for moving a position of the convex lens 112*b* of the objective optical system on the optical axis, and the encoder 119 which detects the number of rotations of the motor 118. A magnification ratio and a focal length of the imaging unit 110 are adjusted according to a manipulation input to the manipulation unit 150 (more specifically, manipulation of the zoom SW 151 and the focus SW 152 shown in FIG. 2). For example, the motor 118 is driven and a focal length of the imaging unit 110 is adjusted according to pressing of the zoom SW 151. The encoder 119 detects the number of rotations of the motor 118, and provides the detection value to an observation point position computation unit 193 of the control unit 190 to be described below. Note that, in the first embodiment, the imaging unit 110 may not be configured as a microscope, but may be configured as another device having an imaging function, such as a camera.

The manipulation unit 150 is an input interface which receives inputs of manipulation of the operator with respect to the medical observation device 10. The manipulation unit 150 is constituted by devices manipulated by the operator, for example, a mouse, a keyboard, a touch panel, buttons, switches, levers, and the like. The operator can input various kinds of information or various instructions to the medical observation device 10 through the manipulation unit 150. The manipulation unit 150 corresponds to the zoom SW 151, the focus SW 152, the all-free SW 153, and the point lock SW 154 in the configuration shown in FIG. 2. When a user presses the zoom SW 151 or the focus SW 152, for example, a magnification ratio or a focal length of the imaging unit 110 can be adjusted according to the manipulation. In addition, when a user presses the all-free SW 153 or the point lock SW 154, the information that the switch has been pressed is provided to an operation mode control unit 191 of the control unit 190 to be described below, and thereby the operation mode of the holding unit (arm unit) of the medical observation device 10 is controlled.

The rotary shaft parts 160 and 170 represent the function corresponding to the members constituting the rotary shafts provided in the holding unit of the medical observation device 10. As described with reference to FIG. 2, the O1 shaft to the O6 shaft of the rotary shafts of the medical observation device 10 can be distinguished as passive shafts and active shafts. The rotary shaft part 160 represents the function of the rotary shaft parts which correspond to the passive shafts (i.e., the rotary shaft parts 210, 250, and 260, and the parallelogrammic link mechanism 240 shown in FIG. 2), and the rotary shaft part 170 represents the function of the rotary shaft parts which correspond to the active shafts (i.e., the rotary shaft parts 220 and 230 shown in FIG. 2). For the sake of convenience in description, the rotary shaft part 160 will also be referred to as a passive rotary shaft part 160, and the rotary shaft part 170 as an active rotary shaft part 170 hereinbelow.

The passive rotary shaft part 160 has a state detection unit 161 and an operation unit 163 as functions. The state detection unit 161 detects a state of the passive rotary shaft part 160, i.e., a rotation angle of the passive rotary shaft part 160. The state detection unit 161 is configured with an encoder 162 which can detect a rotation angle of the rotary shaft part 160. The encoder 162 corresponds to, for example, the encoders 212, 292, 252, and 262 shown in FIG. 2. The state detection unit 161 provides the value of the rotation angle detected by the encoder 162 to an arm-state acquisition unit 192 of the control unit 190 to be described below.

The operation unit 163 has a function related to rotation operations of the passive rotary shaft part 160. The operation unit 163 is configured with a brake 164 which regulates rotation of the passive rotary shaft part 160. As described, the operation unit 163 has no function of actively driving the passive rotary shaft part 160, like an actuator. The brake 164 corresponds to, for example, the brakes 211, 291, 251, and 261 shown in FIG. 2. The operation unit 163 causes the brake 164 to function or releases it according to an operation mode selected through an instruction from the operation mode control unit 191 of the control unit 190 to be described below. Specifically, when the operation mode is the fixed mode, the operation unit 163 causes the brake 164 to function so that the passive rotary shaft part 160 is not freely rotated according to external force. On the other hand, when the operation mode is the all-free mode and the point lock mode, the operation unit 163 releases the brake 164 so that the passive rotary shaft part 160 is freely rotated according to direct manipulation of the operator.

The active rotary shaft part 170 has a state detection unit 171 and an operation unit 173 as functions. The state detection unit 171 detects a state of the active rotary shaft part 170, i.e., a rotation angle of the active rotary shaft part 170. The state detection unit 171 is configured with an encoder 172 which can detect rotation angles of the active rotary shaft part 170. The encoder 172 corresponds to, for example, the encoders 222 and 232 shown in FIGS. 2 and 4. The state detection unit 171 provides the value of a rotation angle detected by the encoder 172 to the arm-state acquisition unit 192 of the control unit 190 to be described below.

The operation unit 173 has a function related to rotation operations of the active rotary shaft part 170. The operation unit 173 is constituted by an actuator 174 which drives rotation of the active rotary shaft part 170 around a rotary shaft and a brake 175 which regulates rotation of the active rotary shaft part 170. As described, the operation unit 173 has a function of actively driving the active rotary shaft part 170, like the actuator 174. The actuator 174 corresponds to, for example, the actuators 223 and 233 shown in FIGS. 2 and 4. In addition, the brake 175 corresponds to, for example, the brakes 221 and 231 shown in FIGS. 2 and 4.

The operation unit 173 causes the brake 175 to function or releases it according to an operation mode selected through an instruction from the operation mode control unit 191 of the control unit 190 to be described below. Specifically, when the operation mode is the fixed mode and the point lock mode, the operation unit 173 causes the brake 175 to function so that the active rotary shaft part 170 is not freely rotated according to external force. On the other hand, when the operation mode is the all-free mode, the operation unit 173 releases the brake 175 so that the active rotary shaft part 170 is freely rotated according to direct manipulation of the operator. In addition, the operation unit 173 drives the actuator 174 according to an instruction from a driving control unit 194 of the control unit 190 to be described below in the point lock mode so that the point lock operation is performed, i.e., the observation point with respect to the imaging unit 110 after movement coincides with the observation point with respect to the imaging unit 110 before movement.

The storage unit 180 is configured with, for example, a magnetic storage device such as a hard disk drive (HDD), a semiconductor storage device, an optical storage device, or a magneto-optical storage device, and stores various kinds of information processed by the medical observation device 10. The storage unit 180 can store, for example, various kinds of information related to control over driving of the holding unit of the medical observation device 10. The various kinds of information related to driving control include various kinds of information, for example, information regarding an internal model corresponding to the holding unit, detection values of the encoder 119 of the imaging unit 110 and detection values of the encoders 162 and 172 of the state detection units 161 and 171, and a state of the arm to be described below, position information of the observation point, information regarding control amounts of the actuator 174 of the operation unit 173, and the like. The control unit 190 is configured to be capable of accessing the storage unit 180, and the control unit 190 can perform various arithmetic processes using the various kinds of information stored in the storage unit 180.

The control unit 190 is configured with, for example, a processor such as a CPU or a DSP, and controls operations of the medical observation device 10 as it operates a predetermined program. Note that the control unit 190 and the storage unit 180 may be realized by the controller 140 shown in FIG. 2. For example, the function of the storage unit 180 may be realized by a storage device such as a memory provided in the controller 140, and the function of the control unit 190 may be realized by the processor provided in the controller 140.

The control unit 190 has the operation mode control unit 191, the arm-state acquisition unit 192, the observation point position computation unit 193, and the driving control unit 194 as functions.

The operation mode control unit 191 controls the operation modes of the holding unit of the medical observation device 10. The operation mode control unit 191 decides an operation mode of the holding unit according to an input of manipulation from the operator via the manipulation unit 150, and issues an instruction to realize the decided operation mode to the operation units 163 and 173 of the rotary shaft parts 160 and 170. When neither the all-free SW 153 nor the point lock SW 154 is pressed, for example, the operation mode control unit 191 decides the operation mode of the holding unit to be the fixed mode, and issues an instruction to cause the brakes 164 and 175 to function to the operation units 163 and 173. In addition, when the all-free SW 153 is pressed, for example, the operation mode control unit 191 decides the operation mode of the holding unit to be the all-free mode, and issues an instruction to release the brakes 164 and 175 to the operation units 163 and 173. Furthermore, when the point lock SW 154 is pressed, for example, the operation mode control unit 191 decides the operation mode of the holding unit to be the point lock mode, issues an instruction to release the brake 164 to the operation unit 163 corresponding to a passive shaft, and issues an instruction to cause the brake 175 to function to the operation unit 173 corresponding to an active shaft.

The arm-state acquisition unit 192 acquires a state of the holding unit (a state of the arm) based on states of the rotary shaft parts 160 and 170. Here, a state of the arm may indicate a position and an attitude of the holding unit 120. The arm-state acquisition unit 192 acquires a state of the arm based on detection values of the encoders 162 and 172 (i.e., rotation angles of the rotary shaft parts 160 and 170) provided from the state detection units 161 and 171, and the internal model stored in the storage unit 180. The internal model includes geometric parameters of the holding unit, i.e., information regarding disposition positions of the rotary shafts of the holding unit, lengths and shapes of the arms 271 to 274, etc., and thus the arm-state acquisition unit 192 can acquire the state of the arm based on the detection values of the encoders 162 and 172 and the internal model. Here, the arm-state acquisition unit 192 acquires the state of the arm at the time point at which the point lock operation has started, and continues acquiring states of the arm while the point lock operation is being performed at all times. The arm-state acquisition unit 192 provides information regarding the state of the arm at the time point at which the point lock operation has started to the observation point position computation unit 193. In addition, the arm-state acquisition unit 192 provides the states of the arm acquired while the point lock operation is being performed to the driving control unit 194.

The observation point position computation unit 193 computes a three-dimensional position of the observation point at the time of the start of the point lock operation. The observation point position computation unit 193 can compute the three-dimensional position of the observation point based on information regarding the state of the arm at the time point at which the point lock operation has started provided from the arm-state acquisition unit 192, i.e., information indicating the position and the attitude of the holding unit and a detection value of the encoder 119 provided from the imaging unit 110. Specifically, the number of rotations of the motor 118 detected by the encoder 119 is a value indicating a position of the convex lens 112*b* of the objective optical system shown in FIG. 3 on the optical axis, and thus the observation point position computation unit 193 can compute a working distance of the imaging unit 110, i.e., a distance from the imaging unit 110 to the observation point based on the detection value of the encoder 119. In addition, the observation point position computation unit 193 can compute a three-dimensional position of the imaging unit 110 attached at the front end of the holding unit based on information regarding the state of the arm. Based on the computed information, the observation point position computation unit 193 can compute the three-dimensional position of the observation point. The three-dimensional position of the observation point can be expressed in, for example, coordinates of the internal model in a coordinate system. The three-dimensional position of the observation point computed by the observation point position computation unit 193 can also be said to indicate a position of the observation point with respect to the holding unit, i.e., a relative positional relation between the holding unit and the observation point. The observation point position computation unit 193 provides the computed position information of the observation point at the time of the start of the point lock operation to the driving control unit 194.

The driving control unit 194 controls driving of the active rotary shaft part 170 performed in the point lock operation. The driving control unit 194 can control driving of the active rotary shaft part 170 based on the position information of the observation point at the time of the start of the point lock operation so that the observation point is positioned on the optical axis of the imaging unit 110, i.e., the observation point with respect to the imaging unit 110 after movement coincides with the observation point with respect to the imaging unit 110 before movement. Specifically, the driving control unit 194 is provided with the three-dimensional position information of the observation point at the time point at which the point lock operation has started from the observation point position computation unit 193. In addition, the driving control unit 194 is provided with information regarding the state of the arm in the point lock operation (i.e., the position and attitude of the holding unit) from the arm-state acquisition unit 192 when necessary. Thus, based on the information, the driving control unit 194 can compute a relative positional relation between the observation point at the time point at which the point lock operation has started and the positions and attitudes of the imaging unit 110 and the holding unit when necessary according to a change in the positions and attitudes of the imaging unit 110 and the holding unit. Based on the computed positional relation, the driving control unit 194 computes a rotation angle (i.e., a control amount when the active rotary shaft part 170 is driven) of the rotary shaft part 170 (i.e., the rotary shaft parts 220 and 230 shown in FIG. 2) at which the observation point at the time of the start of the point lock operation is likely to be positioned on the optical axis of the imaging unit 110 at the position of the imaging unit 110 after the movement. Then, the actuator 174 of the operation unit 173 is driven to realize the rotation angle. As driving of the active rotary shaft part 170 is controlled according to the control amount computed by the driving control unit 194, the point lock operation is realized. Note that, when the driving control unit 194 computes the control amount, for example, a generally used position control theory can be applied, and thus detailed description thereof is omitted.

The functional configuration of the medical observation device 10 according to the first embodiment has been described above with reference to FIG. 5.

3. Second Embodiment

Next, a second embodiment of the present disclosure will be described. The second embodiment corresponds to one in which the configuration of the rotary shaft parts corresponding to active shafts of the first embodiment is changed and accordingly the method for controlling the rotary shaft parts in the point lock mode is changed. Other configurations are similar to those of the first embodiment, and thus differences from the first embodiment will be mainly described in the following description of the second embodiment, and detailed description regarding overlapping matter with respect to the first embodiment will be omitted.

(3-1. Configuration of Device)

Figure 6:
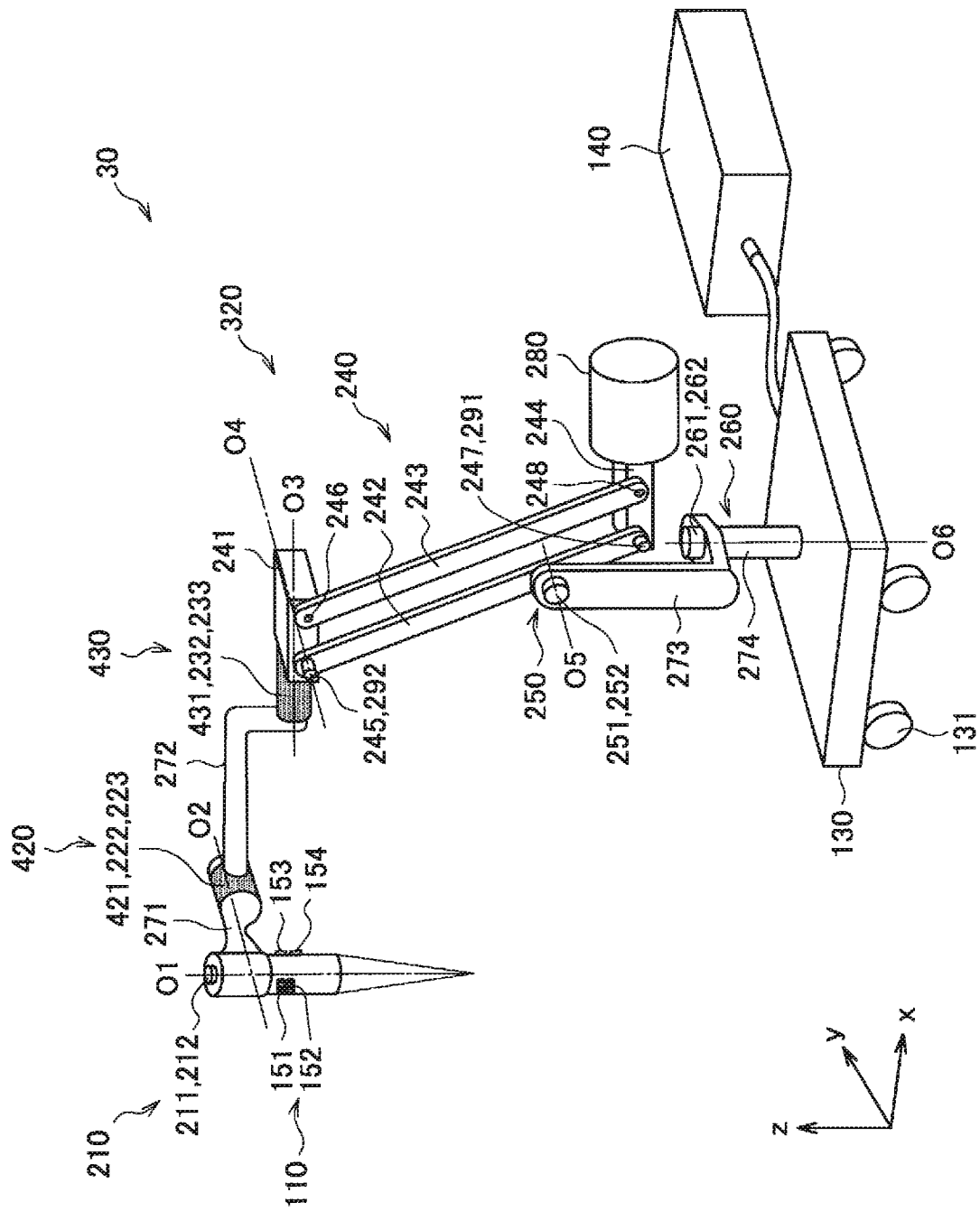
FIG. 6 is a diagram showing an example of a configuration of a medical observation device according to a second embodiment of the present disclosure.
Figure 7:
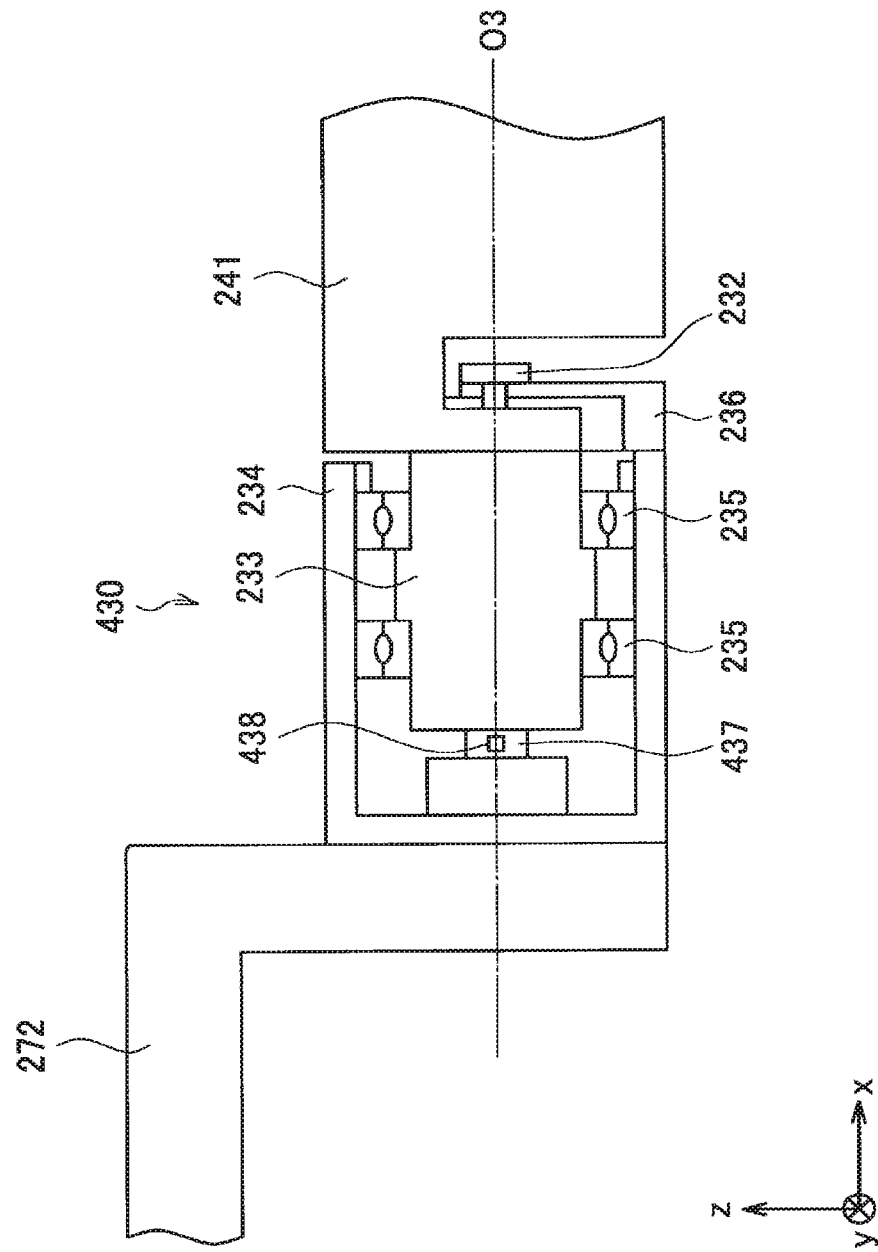
FIG. 7 is a diagram showing an example of a configuration of a rotary shaft part corresponding to an active shaft of the rotary shaft part shown in FIG. 6.

A configuration of a medical observation device according to the second embodiment of the present disclosure will be described with reference to FIGS. 6 and 7. FIG. 6 is a diagram showing an example of the configuration of the medical observation device according to the second embodiment of the present disclosure. FIG. 7 is a diagram showing an example of a configuration of a rotary shaft part corresponding to an active shaft of the rotary shaft part shown in FIG. 6

Referring to FIG. 6, the medical observation device 30 according to the second embodiment includes an imaging unit 110, a holding unit 320 (an arm unit 320), a base 130 (a base 130), and a controller 140. Note that since the constituent elements other than the holding unit 320 are similar to those of the medical observation device 10 according to the first embodiment described with reference to FIG. 2, description thereof will be omitted.

The holding unit 320 holds the imaging unit 110, moves the imaging unit 110 three-dimensionally, and fixes a position and an attitude of the imaging unit 110 after movement. As shown in FIG. 6, the holding unit 320 according to the second embodiment corresponds to one in which the rotary shaft parts 220 and 230 which correspond to active shafts in the holding unit 120 according to the first embodiment shown in FIG. 2 change to rotary shaft parts 420 and 430 respectively. Since other constituent elements thereof are similar to those of the holding unit 120, detailed description will be omitted.

In the second embodiment, the O2 shaft and the O3 shaft can function as active shafts corresponding to the rotary shaft parts 420 and 430 as in the first embodiment. However, specific configurations of the rotary shaft parts 420 and 430 are different from those of the first embodiment. Specifically, the rotary shaft parts 420 and 430 have force sensors 421 and 431, and actuators 223 and 233 respectively.

Configurations of the rotary shaft parts 420 and 430 will be described, exemplifying the rotary shaft part 430 with reference to FIG. 7. FIG. 7 shows a cross-sectional diagram of the rotary shaft part 430 viewed in a plane that passes through a rotary shaft (the O3 shaft). Referring to FIG. 7, the rotary shaft part 430 corresponds to one in which the brake 231 is not provided in the rotary shaft part 230 shown in FIG. 4 and a strain gauge 438 is provided in a transmission member 437 which transmits outputs of the actuator 233 to a member of the subsequent stage. Since other constituent elements are similar to those of the rotary shaft part 230, detailed description will be omitted.

The transmission member 437 has a function of transmitting outputs of the actuator 233 to the housing 234 which acts as a rotation body of an output side. The strain gauge 438 is affixed to a surface of the transmission member 437. The strain gauge 438 can detect force applied to the transmission member 437 as a stress value (a torque value). For example, the strain gauge 438 can detect external force exerted on the rotary shaft part 430 according to rotation of the housing 234 and the arm 272. The external force can be, for example, external force exerted on the rotary shaft part 430 when an operator manually moves the imaging unit 110. As described above, the strain gauge 438 functions as a force sensor which detects external force on the rotary shaft part 430, and corresponds to the above-described force sensor 431. Note that a specific configuration corresponding to the force sensor 431 is not limited to the strain gauge 438. In the second embodiment, a device which can detect a stress value applied to the transmission member 437 may be provided, and as the device, any of various known stress detection devices that are not limited to a strain gauge can be applied.

Differently from the rotary shaft part 230, no mechanical brake mechanism is provided in the rotary shaft part 430. As the controller 140 appropriately controls driving of the actuator 233 in the rotary shaft part 430, brake control can function. For example, when it is desired to regulate rotation of the rotary shaft part 430 as in the fixed mode, control to prevent an output shaft of the actuator 233 from rotating is performed, without driving the actuator 233. Accordingly, the housing 234 connected to the output shaft of the actuator 233 does not rotate, and thus rotation of the rotary shaft part 430 is fixed.

In addition, when the rotary shaft part 430 rotates, driving of the rotary shaft part 430 can be controlled by the controller 140 in so-called force control in which force is set to a control target value. For example, in the all-free mode, driving of the actuator 233 is controlled based on a detection value of the strain gauge 438 such that the detection value of the strain gauge 438 becomes substantially zero (i.e., such that external force exerted to rotate the rotary shaft part 430 is negated). Accordingly, as the rotary shaft part 430 is smoothly rotated in a state of substantially no resistance according to direct manual manipulation of the operator, the O3 shaft corresponding to the rotary shaft part 430 acts as if it were a passive shaft. In addition, in the point lock mode, driving of the actuator 233 is controlled such that an observation point is positioned on the optical axis of the imaging unit 110 at all times, in other words, the observation point with respect to the imaging unit 110 after movement coincides with the observation point with respect to the imaging unit 110 before movement. Here, as shown in FIG. 6, the medical observation device 30 according to the second embodiment can also be configured as a so-called balance arm having a counterweight 280, as in the first embodiment. Thus, in the point lock mode, the operator can move the imaging unit 110 with light force, feeling as if it were weightless while realizing a point lock operation using force control, and thus a manipulation property for a user can be enhanced.

The configuration of the medical observation device 30 according to the second embodiment has been described above with reference to FIGS. 6 and 7. Note that, although the configuration of the rotary shaft part 430 has been described above with reference to FIG. 7 as an example in order to describe the rotary shaft parts 420 and 430 corresponding to active shafts, the rotary shaft part 420 has a configuration similar to that of the rotary shaft part 430, and can perform similar operations in the respective operation modes as well.

(3-2. Operation in Use)

Next, an operation in use of the medical observation device 30 according to the second embodiment will be described. Note that manipulation performed by an operator in the operation in use of the medical observation device 30 according to the second embodiment is substantially similar to the manipulation of the operator for the operation in use of the medical observation device 10 according to the first embodiment described in (2-2. Operation in use) above. In the second embodiment, however, control methods of the rotary shaft parts 420 and 430 corresponding to active shafts in the all-free mode and the point lock mode are different from those in the first embodiment.

Manipulation performed from moving of the medical observation device 30 close to an operating table to pressing of the all-free SW 153 is similar to that of the first embodiment. When the all-free SW 153 is pressed, brakes 211, 291, 251, and 261 of rotary shaft parts 210, 420, 430, 250, and 260 and a parallelogrammic link mechanism 240 are released, thus the operator performs direct manual manipulation, and thereby the imaging unit 110 can be freely moved. Here, releasing the brakes of the rotary shaft parts 210, 250, and 260, and the parallelogrammic link mechanism 240 corresponding to passive shafts is similar to that of the first embodiment. On the other hand, with regard to the rotary shaft parts 420 and 430 in the second embodiment, driving of the actuators 223 and 233 (for example, the actuator 233 shown in FIG. 7) of the rotary shaft parts 420 and 430 is controlled such that detection values of the force sensors 421 and 431 (for example, the strain gauge 438 shown in FIG. 7) mounted in the rotary shaft parts 420 and 430 become substantially zero while the all-free SW 153 is being pressed. Accordingly, while the all-free SW 153 is being pressed, i.e., in the all-free mode, all rotary shafts including the O2 shaft and the O3 shaft corresponding to the rotary shaft parts 420 and 430 act as passive shafts which rotate according to direct manipulation of the operator. Note that control over driving of the rotary shaft parts 420 and 430 described above can be executed based on, for example, a general force control theory.

The operator moves the imaging unit 110 in the state with the all-free SW 153 pressed while viewing an image photographed by the imaging unit 110 and displayed on a display device so that an operation site is positioned within the visual field of the imaging unit 110. Since the medical observation device 30 is a balance arm as in the first embodiment, and the above-described driving control to cause the rotary shaft parts 420 and 430 to function as passive shafts is performed, the operator can easily move the imaging unit 110 with light force.

The operator releases the all-free SW 153 after the imaging unit 110 is moved to a proper position. Accordingly, the brakes 211, 291, 251, and 261 of the respective rotary shaft parts 210, 420, 430, 250, and 260, and parallelogrammic link mechanism 240 function, and the operation mode of the holding unit 320 transitions to the fixed mode. In the fixed mode, the operator appropriately adjusts a magnification ratio and a focal length of an image captured by the imaging unit 110 using the zoom SW 151 and the focus SW 152, and then performs various kinds of treatment on the operation site while viewing the captured image. Here, the brake mechanism of the rotary shaft parts 210, 250, and 260, and the parallelogrammic link mechanism 240 which correspond to passive shafts is similar to that of the first embodiment. On the other hand, with regard to the rotary shaft parts 420 and 430 which correspond to active shafts in the second embodiment, driving of the actuators 223 and 233 mounted in the rotary shaft parts 420 and 430 is controlled such that the rotary shaft parts 420 and 430 do not rotate, and thus their rotation is fixed.

When it is desired to perform the point lock operation, i.e., when it is desired to observe the observation point from different direction with the observation point fixed, the operator presses the point lock SW 154. While the point lock SW 154 is being pressed, the brakes 211, 291, 251, and 261 of the rotary shaft parts 210, 250, and 260, and the parallelogrammic link mechanism 240 which correspond to passive shafts are released. In addition, driving of the actuators 223 and 233 of the rotary shaft parts 420 and 430 corresponding to active shafts is controlled such that the observation point is positioned on the optical axis of the imaging unit 110 at all times.

The control over driving of the rotary shaft parts 420 and 430 in the point lock operation as described above can be executed by the controller 140 shown in FIG. 6. As in the first embodiment, the controller 140 monitors detection values of the encoder 119 provided in the objective optical system of the imaging unit 110 and detection values of encoders 212 to 262 of the rotary shaft parts 210, 420, 430, 250, and 260, and the parallelogrammic link mechanism 240 at all times. Based on the detection values of the encoders 119 and 212 to 262, the controller 140 calculates a three-dimensional position of the observation point with respect to the holding unit 320 at the time point at which the point lock SW 154 was pressed. In addition, when the operator attempts to move the imaging unit 110 with the point lock SW 154 pressed, the controller 140 computes changes in positions and attitudes of the imaging unit 110 and the holding unit 320 during the movement based on the detection values of the encoders 212 to 262 of the rotary shaft parts 210, 420, 430, 250, and 260 and the parallelogrammic link mechanism 240 when necessary. As described above, the controller 140 can detect a three-dimensional position of the observation point with respect to the holding unit 320 at the time point at which the point lock SW 154 was pressed at all times when positions and attitudes of the imaging unit 110 and the holding unit 320 are changed. Based on the information, the controller 140 executes the point lock operation in which the observation point at the time point at which the point lock SW 154 is pressed is set as a reference point (a point-lock point). To be specific, based on three-dimensional position information of the detected point-lock point with respect to the holding unit 320, the controller 140 can control driving of the actuators 223 and 233 of the rotary shaft parts 420 and 430 such that the optical axis of the imaging unit 110 passes through the observation point at all times before and after the change of the position of the imaging unit 110.

When the operator moves the imaging unit 110 while the point lock SW 154 is being pressed, i.e., during the point lock operation, as described above, rotation around the O1 shaft, the O4 shaft, the O5 shaft, and the O6 shaft which are passive shafts is performed through the manipulation of the operator, and thus rotation around the optical axis and three-dimensional translational movement of the imaging unit 110 is performed. On the other hand, a relative positional relation between the observation point and the imaging unit 110 and the holding unit 320 after the movement is computed from movement amounts (rotation amounts) of these passive shafts, and based on the computed information, rotation around the O2 shaft and the O3 shaft which are active shafts, i.e., tilting movement of the imaging unit 110, is controlled such that the optical axis passes through the observation point. Accordingly, even if the operator moves the position of the imaging unit 110 loosely, the imaging unit 110 is tilted facing the observation point at all times, without losing sight of the observation point.

When the imaging unit 110 is moved to a desired position, the operator releases the point lock SW 154 to cause the operation mode of the holding unit 320 to transition to the fixed mode, and thereby the position of the imaging unit 110 is fixed. Observing the operation site from different directions, the operator can perform proper treatment on the operation site.

The operation in use of the medical observation device 30 according to the second embodiment has been described above. According to the second embodiment, the force sensors are provided in the rotary shaft parts 420 and 430 which correspond to active shafts, and driving of the rotary shaft parts 420 and 430 is controlled through force control based on detection values of the force sensors as described above, and thus an excellent manipulation property in the point lock operation as in the first embodiment can be obtained.

Note that, in the second embodiment, the following control can also be executed by performing control over driving of the rotary shaft parts 420 and 430 through force control. For example, an operation mode may be switched according to the magnitude of external force exerted on the imaging unit 110. To be specific, when an external force greater than a predetermined value is exerted on the imaging unit 110 and the force sensors 421 and 431 of the rotary shaft parts 420 and 430 detect an external force greater than a predetermined value in the point lock mode, the operation mode may be switched to the all-free mode. Accordingly, when an operator wants to perform fine adjustment of a position of the observation point in the point lock operation, for example, he or she can change the operation mode to the all-free mode temporarily by directly performing manipulation to move the imaging unit 110 with a certain degree of force or more, without deliberately performing an input of manipulation using the manipulation unit 150, and thus can move the imaging unit 110 to a desired position, having no regulation of point lock. When direct manipulation on the imaging unit 110 is finished, the operation mode is automatically switched to the point lock mode again. Through this control, while the point lock operation is performed, the imaging unit 110 can be moved within the x-y plane with simpler manipulation, a positional relation between the optical axis of the imaging unit 110 and the observation point can be finely adjusted, and thus convenience of the operator can be enhanced.

(3-3. Functional Configuration of Device)

Figure 8:
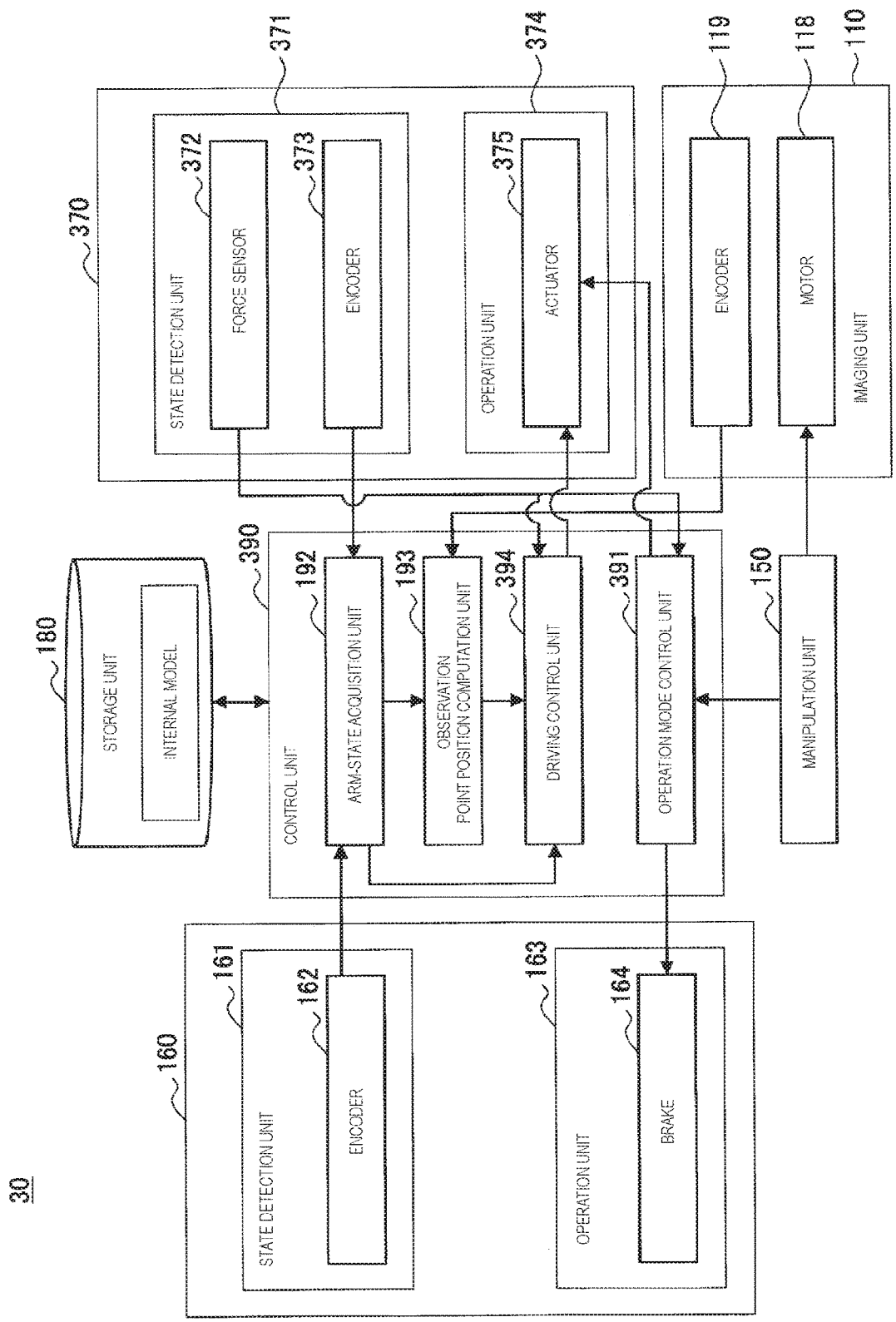
FIG. 8 is a functional block diagram showing an example of a functional configuration of the medical observation device according to the second embodiment.

Next, a functional configuration of the medical observation device 30 according to the second embodiment described with reference to FIG. 6 will be described with reference to FIG. 8. FIG. 8 is a functional block diagram showing an example of the functional configuration of the medical observation device 30 according to the second embodiment. Note that the functional configuration of the medical observation device 30 according to the second embodiment corresponds to one in which the functional configurations of the active rotary shaft part 170 and the control unit 190 are changed from those of the medical observation device 10 according to the first embodiment shown in FIG. 5. Thus, functions of the functional configuration of the medical observation device 30 different from those of the first embodiment will be mainly described.

Referring to FIG. 8, the medical observation device 30 includes the imaging unit 110, the manipulation unit 150, a passive rotary shaft part 160, an active rotary shaft part 370, a storage unit 180, and a control unit 390. Here, since functions of the imaging unit 110, the manipulation unit 150, the passive rotary shaft part 160, and the storage unit 180 are similar to those of the constituent elements of the medical observation device 10 shown in FIG. 5, detailed description thereof will be omitted.

The active rotary shaft part 370 has a state detection unit 371 and an operation unit 374 as functions. The state detection unit 371 detects a state of the active rotary shaft part 370, i.e., external force exerted on the active rotary shaft part 370 and a rotation angle of the active rotary shaft part 370. The state detection unit 371 is constituted by a force sensor 372 which can detect external force exerted on the active rotary shaft part 370 and an encoder 373 which can detect rotation angles of the active rotary shaft part 370. The force sensor 372 corresponds to, for example, the force sensors 421 and 431 shown in FIG. 6 and the strain gauge 438 shown in FIG. 7, and can detect external force exerted on the active rotary shaft part 370 as a stress value (a torque value). In addition, the encoder 373 corresponds to, for example, encoders 222 and 232 shown in FIGS. 6 and 7. The state detection unit 371 provides a stress value detected by the force sensor 372 to an operation mode control unit 391 and a driving control unit 394 of the control unit 390 to be described below. In addition, the state detection unit 371 provides the value of a rotation angle detected by the encoder 373 to an arm-state acquisition unit 192 of the control unit 390 to be described below.

The operation unit 374 has a function related to rotation operations of the active rotary shaft part 370. The operation unit 374 is constituted by an actuator 375 which drives rotation of the active rotary shaft part 370 around a rotary shaft. The actuator 375 corresponds to, for example, the actuators 223 and 233 shown in FIGS. 6 and 7.

The operation unit 374 drives the actuator 375 according to an operation mode selected through an instruction from the operation mode control unit 391 of the control unit 390 to be described below. To be specific, when the operation mode is the fixed mode, the operation unit 374 stops driving of the actuator 375 such that the actuator 375 is caused not to rotate, and thereby causes the active rotary shaft part 370 not to freely rotate according to external force. On the other hand, when the operation mode is the all-free mode, the operation unit 374 drives the actuator 375 such that a detection value of the force sensor 372 becomes substantially zero, i.e., such that external force exerted on the active rotary shaft part 370 is negated. Accordingly, the active rotary shaft part 370 can be freely rotated according to direct manual manipulation of the operator. In addition, when the operation mode is the point lock mode, the operation unit 374 drives the actuator 375 according to an instruction from the driving control unit 394 of the control unit 390 to be described below so that the point lock operation is performed, i.e., the observation point with respect to the imaging unit 110 after movement coincides with the observation point with respect to the imaging unit 110 before movement.

The control unit 390 is configured with, for example, a processor such as a CPU or a DSP, and controls operations of the medical observation device 30 as it operates a predetermined program. Note that the control unit 390 and the storage unit 180 may be realized by the controller 140 shown in FIG. 6. For example, the function of the storage unit 180 may be realized by a storage device such as a memory provided in the controller 140, and the function of the control unit 390 may be realized by the processor provided in the controller 140.

The control unit 390 has the operation mode control unit 391, the arm-state acquisition unit 192, an observation point position computation unit 193, and the driving control unit 394 as functions. Here, since functions of the arm-state acquisition unit 192 and the observation point position computation unit 193 are similar to those of the constituent elements of the medical observation device 10 shown in FIG. 5, detailed description thereof will be omitted.

The operation mode control unit 391 controls operation modes of the holding unit of the medical observation device 30. The operation mode control unit 391 decides an operation mode of the holding unit according to an input of manipulation performed by the operator using the manipulation unit 150, and issues an instruction to the operation units 163 and 374 of the passive rotary shaft part 160 and the active rotary shaft part 370 to realize the decided operation mode. When neither the all-free SW 153 nor the point lock SW 154 is pressed, for example, the operation mode control unit 391 decides the operation mode of the holding unit to be the fixed mode, issues an instruction to the operation unit 163 to cause the brake 164 to function, and issues an instruction to the operation unit 374 to cause the actuator 375 not to rotate. In addition, when the all-free SW 153 is pressed, for example, the operation mode control unit 391 decides the operation mode of the holding unit to be the all-free mode, issues an instruction to the operation unit 163 to release the brake 164, and issues an instruction to the operation unit 374 to drive the actuator 375 so that a detection value of the force sensor 372 becomes substantially zero. In addition, when the point lock SW 154 is pressed, for example, the operation mode control unit 391 decides the operation mode of the holding unit to be the point lock mode, issues an instruction to the operation unit 163 to release the brake 164, and issues an instruction to the operation unit 374 to drive the actuator 375 to realize the point lock operation according to control of the driving control unit 394. Since a generally used force control theory can be applied to control over driving of the actuator 375 in the all-free mode and the point lock mode, detailed description thereof will be omitted.

In addition, in the second embodiment, the operation mode control unit 391 may decide an operation mode of the holding unit based on external force imposed on the active rotary shaft part 370 detected by the force sensor 372. When, for example, external force imposed on the active rotary shaft part 370 exceeds a predetermined value in the point lock mode, the operation mode control unit 391 may switch the operation mode to the all-free mode. By performing such control, while the point lock operation is performed, the imaging unit 110 can be moved in parallel within the x-y plane through simpler manipulation, thus a positional relation between the optical axis of the imaging unit 110 and the observation point can be finely adjusted, and thus convenience of the operator can be improved.

The driving control unit 394 controls driving of the active rotary shaft part 370 performed in the point lock operation. The driving control unit 394 can control driving of the active rotary shaft part 370 based on the position information of the observation point at the time of the start of the point lock operation so that the observation point is positioned on the optical axis of the imaging unit 110. Specifically, the driving control unit 394 is provided with the three-dimensional position information of the observation point at the time point at which the point lock operation has started from the observation point position computation unit 193. In addition, the driving control unit 394 is provided with information regarding the state of the arm in the point lock operation (i.e., the position and attitude of the holding unit) from the arm-state acquisition unit 192 when necessary. Thus, based on the information, the driving control unit 394 can compute a relative positional relation between the observation point at the time point at which the point lock operation has started and the positions and attitudes of the imaging unit 110 and the holding unit when necessary according to a change in the positions and attitudes of the imaging unit 110 and the holding unit. Based on the computed positional relation, the driving control unit 394 computes a torque value (i.e., a control amount when the active rotary shaft part 370 is driven) for driving the active rotary shaft part 370 (i.e., the rotary shaft parts 420 and 430 shown in FIG. 6) at which the observation point at the time of the start of the point lock operation is likely to be positioned on the optical axis of the imaging unit 110 at the position of the imaging unit 110 after the movement. Then, the actuator 375 of the operation unit 374 is driven to realize the torque value. As driving of the active rotary shaft part 370 is controlled according to the control amount computed by the driving control unit 394, the point lock operation is realized. Note that, when the driving control unit 394 computes the above control amount, for example, a generally used force control theory can be applied, and thus detailed description thereof is omitted.

The functional configuration of the medical observation device 30 according to the second embodiment has been described above with reference to FIG. 8.

4. Third Embodiment

Next, a third embodiment of the present disclosure will be described. The third embodiment corresponds to one in which the configuration of the parallelogrammic link mechanism 240 which functions as a passive shaft in the second embodiment is changed to a configuration corresponding to an active shaft. Other configurations are similar to those of the second embodiment, and thus differences of the third embodiment from the second embodiment will be mainly described below, and detailed description of overlapping matter with respect to the second embodiment will be omitted.

(4-1. Configuration of Device)

Figure 9:
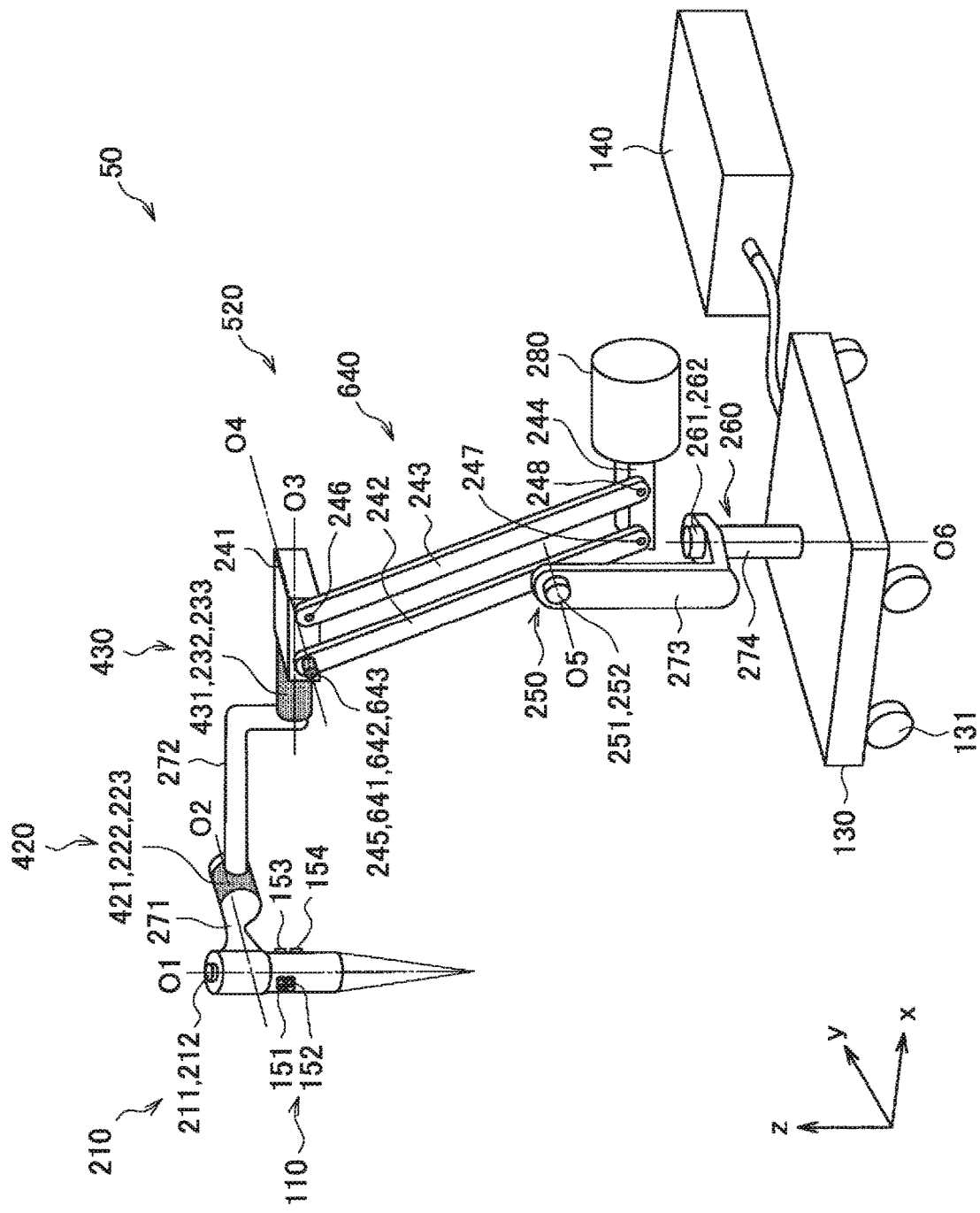
FIG. 9 is a diagram showing an example of a configuration of a medical observation device according to a third embodiment of the present disclosure.

A configuration of a medical observation device according to the third embodiment will be described with reference to FIG. 9. FIG. 9 is a diagram showing an example of the configuration of the medical observation device according to the third embodiment of the present disclosure.

Referring to FIG. 9, the medical observation device 50 according to the third embodiment includes an imaging unit 110, a holding unit 520 (an arm unit 520), a base 130 (a base 130), and a controller 140. Note that since the constituent elements other than the holding unit 520 are similar to those of the medical observation devices 10 and 30 according to the first and second embodiments described with reference to FIGS. 2 and 6, respectively, description thereof will be omitted.

The holding unit 520 holds the imaging unit 110, moves the imaging unit 110 three-dimensionally, and fixes a position and an attitude of the imaging unit 110 after movement. As shown in FIG. 9, the holding unit 520 according to the third embodiment corresponds to one changed from the configuration of the parallelogrammic link mechanism 240 of the holding unit 320 according to the second embodiment shown in FIG. 6. To be specific, while the parallelogrammic link mechanism 240 functions as a passive shaft in the first and second embodiments, a parallelogrammic link mechanism 640 according to the third embodiment functions as an active shaft. Other configurations of the holding unit 520 are similar to those of the holding unit 320, and thus detailed description thereof will be omitted.

Referring to FIG. 9, shapes and disposition of arms 241 to 244 and shaft bearings 245 to 248 of the parallelogrammic link mechanism 640 may be similar to those of the parallelogrammic link mechanism 240 of the first and second embodiments. However, in the third embodiment, similar configurations of rotary shaft parts 420 and 430, i.e., a force sensor 641, an encoder 642, and an actuator 643 are provided for the shaft bearings 245 to 248 of the parallelogrammic link mechanism 640. Accordingly, the parallelogrammic link mechanism 640 can function as an active shaft. In the example shown in FIG. 9, the force sensor 641, the encoder 642, and the actuator 643 are provided in the shaft bearing 245. However, disposition positions of the force sensor 641, the encoder 642, and the actuator 643 are not limited thereto, and these members may be provided in any of the shaft bearings 245 to 248.

In the third embodiment, the parallelogrammic link mechanism 640 is driven according to control of the controller 140. For example, as the controller 140 appropriately controls driving of the actuator 643 of the parallelogrammic link mechanism 640, brake control can function. When it is desired to regulate rotation of the parallelogrammic link mechanism 640 as in the fixed mode, control is performed such that the actuator 643 is not driven and thus an output shaft of the actuator 643 is not rotated.

In addition, when the parallelogrammic link mechanism 640 is rotated, driving of the parallelogrammic link mechanism 640 can be controlled by the controller 140 in so-called force control in which force is set to a control target value. In the all-free mode, for example, driving of the actuator 643 is controlled based on a detection value of the force sensor 641 so that the detection value of the force sensor 641 becomes substantially zero (i.e., so that force exerted from an outside to rotate the parallelogrammic link mechanism 640 is negated). Accordingly, as the parallelogrammic link mechanism 640 is smoothly rotated in a state of substantially no resistance according to direct manual manipulation of an operator, the O4 shaft corresponding to the parallelogrammic link mechanism 640 acts as if it were a passive shaft. In addition, in the point lock mode, driving of the actuator 643 is controlled such that the distance between an observation point and the imaging unit 110 is maintained to a predetermined distance.

The configuration of the medical observation device 50 according to the third embodiment of the present invention has been described with reference to FIG. 9. By employing the above-described configuration, in the medical observation device 50, rotary shafts which correspond to the rotary shaft parts 420 and 430 and the parallelogrammic link mechanism 640 (i.e., the O2 shaft, the O3 shaft, and the O4 shaft) function as active shafts, and rotary shafts which correspond to the rotary shaft parts 210, 250, and 260 (i.e., the O1 shaft, the O5 shaft, and the O6 shaft) function as passive shafts. Here, as described in (2-1. Configuration of device), the O2 shaft and the O3 shaft which are rotary shafts corresponding to the rotary shaft parts 420 and 430 can be said to be two shafts which can decide a tilt of the imaging unit 110, i.e., the optical axis direction of the imaging unit 110. Thus, as rotation around the O2 shaft and the O3 shaft is controlled, an operation to cause the imaging unit 110 to face the direction of the observation point, i.e., the point lock operation, can be performed regardless of positions of the imaging unit 110. On the other hand, as shown in FIG. 9, the O4 shaft which is a rotary shaft corresponding to the parallelogrammic link mechanism 640 can be said to be a shaft which can decide a position of the imaging unit 110 in the z axis direction, i.e., a distance between the imaging unit 110 and the observation point. As described above, as the third embodiment is configured such that the O2 shaft, the O3 shaft, and the O4 shaft function as active shafts, the point lock operation in which a distance between the observation point and the imaging unit 110 is controlled can be performed.

(4-2. Operation in Use)

Next, an operation in use of the medical observation device 50 according to the third embodiment will be described. Note that manipulation of an operator to operate the medical observation device 50 according to the third embodiment performed by in its use is substantially similar to the manipulation of an operator to operate the medical observation devices 10 and 30 according to the first and second embodiments in their use described in (2-2. Operation in use) and (3-2. Operation in use) above. The third embodiment, however, is different from the first and second embodiments in that drive of the parallelogrammic link mechanism 640 is controlled in each operation mode as the parallelogrammic link mechanism 640 acts as an active shaft in addition to the rotary shaft parts 420 and 430.

Manipulation performed from moving of the medical observation device 50 close to an operating table to pressing of the all-free SW 153 is similar to that of the first and second embodiments. When the all-free SW 153 is pressed, brakes 211, 251, and 261 of rotary shaft parts 210, 420, 430, 250, and 260 and the parallelogrammic link mechanism 640 are released, thus, the operator can freely move the imaging unit 110 through direct manual manipulation. Here, releasing the brakes of the rotary shaft parts 210, 250, and 260 corresponding to passive shafts is similar to that of the first and second embodiments. On the other hand, with regard to the rotary shaft parts 420 and 430 and the parallelogrammic link mechanism 640 which correspond to active shafts in the third embodiment, drive of the actuators 223, 233, and 643 of the rotary shaft parts 420 and 430, and the parallelogrammic link mechanism 640 is controlled such that detection values of the force sensors 421, 431, and 641 mounted in the rotary shaft parts 420 and 430, and the parallelogrammic link mechanism 640 become substantially zero while the all-free SW 153 is being pressed. Accordingly, while the all-free SW 153 is being pressed, i.e., in the all-free mode, all rotary shafts including the O2 shaft, the O3 shaft, and the O4 shaft corresponding to the rotary shaft parts 420 and 430, and the parallelogrammic link mechanism 640 act as passive shafts which rotate according to direct manipulation of the operator. Note that control over driving of the rotary shaft parts 420 and 430, and the parallelogrammic link mechanism 640 described above can be executed based on, for example, a general force control theory.

The operator moves the imaging unit 110 in the state in which the all-free SW 153 is pressed while viewing an image photographed by the imaging unit 110 displayed on, for example, a display device so that an operation site is positioned within the visual field of the imaging unit 110. The medical observation device 50 is a balance arm as in the first and second embodiments, and through the above-described driving control to cause the rotary shaft parts 420 and 430, and the parallelogrammic link mechanism 640 to function as passive shafts, the operator can easily move the imaging unit 110 with light force.

After moving the imaging unit 110 to a proper position, the operator releases the all-free SW 153. Accordingly, the brakes 211, 251, and 261 of the respective rotary shaft parts 210, 420, 430, 250, and 260, and the parallelogrammic link mechanism 640 function, and the operation mode of the holding unit 520 transitions to a fixed mode. In the fixed mode, the operator appropriately adjusts a magnification ratio and a focal length of the image captured by the imaging unit 110 by using the zoom SW 151 and the focus SW 152, and then performs various kinds of treatment on the operation site, viewing the captured image. Here, the brake function of the rotary shaft parts 210, 250, and 260 which correspond to passive shafts is similar to those of the first and second embodiments. On the other hand, with regard to the rotary shaft parts 420 and 430 and the parallelogrammic link mechanism 640 which correspond to active shafts in the third embodiment, driving of the actuators 223, 233, and 643 mounted in the rotary shaft parts 420 and 430 and the parallelogrammic link mechanism 640 is controlled to prevent rotation of the rotary shaft parts 420 and 430 and the parallelogrammic link mechanism 640, and thus their rotation is fixed.

When the operator wants to perform a point lock operation, in other words, when he or she wants to observe an observation point from a different direction with the observation point fixed, the operator presses the point lock SW 154. While the point lock SW 154 is being pressed, the brakes 211, 251, and 261 of the rotary shaft parts 210, 250, and 260 which correspond to passive shafts are released. In addition, with regard to the rotary shaft parts 420 and 430, and the parallelogrammic link mechanism 640 which correspond to active shafts, driving of the actuators 223, 233, and 643 is controlled to realize the point lock operation. Specifically, driving of the actuators 223 and 233 of the rotary shaft parts 420 and 430 is controlled such that the observation point is positioned on the optical axis of the imaging unit 110 at all times. In addition, with regard to the parallelogrammic link mechanism 640, driving of the actuator 643 of the parallelogrammic link mechanism 640 is controlled such that a distance between the observation point and the imaging unit 110 is maintained to be constant.

The control over driving of the rotary shaft parts 420 and 430 and the parallelogrammic link mechanism 640 during the point lock operation as described above can be executed by the controller 140 shown in FIG. 9. As in the first and second embodiments, the controller 140 monitors a detection value of the encoder 119 provided in an objective optical system of the imaging unit 110 and detection values of the encoders 212, 222, 232, 642, 252, and 262 of the rotary shaft parts 210, 420, 430, 250, and 260, and the parallelogrammic link mechanism 640 at all times. Based on the detection values of the respective encoders 119, 212, 222, 232, 642, 252, and 262, the controller 140 calculates a three-dimensional position of the observation point with respect to the holding unit 320 at the time point at which the point lock SW 154 is pressed. In addition, if the operator attempts to move the imaging unit 110 while the point lock SW 154 is being pressed, the controller 140 computes a change in a position and attitude of the moving imaging unit 110 and holding unit 520 based on detection values of the encoders 212, 222, 232, 642, 252, and 262 of the rotary shaft parts 210, 420, 430, 250, and 260, and the parallelogrammic link mechanism 640 when necessary. As described above, when there is a change in a position and attitude of the imaging unit 110 and the holding unit 520, the controller 140 can detect a three-dimensional position of the observation point with respect to the holding unit 520 at the time point at which the point lock SW 154 is pressed at all times. Based on the information, the controller 140 allows the point lock operation to be executed in which a distance, of which a reference point (a point-lock point) is set to the observation point at the time point at which the point lock SW 154 is pressed, is maintained to be substantially constant. To be specific, the controller 140 controls driving of the actuators 223, 233, and 643 of the rotary shaft parts 420 and 430 based on the information of the three-dimensional position of the detected point-lock point with respect to the holding unit 520 such that the optical axis of the imaging unit 110 passes through the point-lock point at all times, and a distance between the point-lock point and the imaging unit 110 is maintained to be constant before and after the change in the position of the imaging unit 110.

When the operator moves the imaging unit 110 while the point lock SW 154 is being pressed, in other words, during the point lock operation, as described above, rotation of the O1 shaft, the O5 shaft, and the O6 shaft which are passive shafts is performed according to manipulation of the operator, and rotation around the optical axis of the imaging unit 110 and three-dimensional translational movement are performed. On the other hand, a relative positional relation between the observation point and the imaging unit 110 and the holding unit 520 after the movement is computed from a movement amount (a rotation amount) of these passive shafts, and based on the computed information, rotation around the O2 shaft and the O3 shaft which are active shafts, i.e., tilting movement of the imaging unit 110, is controlled such that the optical axis passes through the observation point. Furthermore, based on the movement amount of the imaging unit 110 resulting from the rotation around the O5 shaft and the O6 shaft, rotation around the O4 shaft is controlled such that the distance between the observation point and the imaging unit 110 is maintained to be constant, in other words, the imaging unit 110 moves on a surface of a sphere of which the radius is set to the distance between the observation point and the imaging unit 110 (i.e., a working distance) at the time point at which the point lock SW 154 is pressed. Accordingly, even if the operator moves the position of the imaging unit 110 loosely, the imaging unit 110 is moved such that a working distance remains constant while facing the observation point at all times, without losing sight of the observation point.

When the imaging unit 110 is moved to a desired position, the operator releases the point lock SW 154 to cause the operation mode of the holding unit 320 to transition to the fixed mode, and thereby the position of the imaging unit 110 is fixed. Observing the operation site from different directions, the operator can perform proper treatment on the operation site.

The operation in use of the medical observation device 50 according to the third embodiment has been described above. According to the third embodiment, the point lock operation involving the distance between the observation point and the imaging unit 110 can be executed. Since the point lock operation can be performed in the state in which a distance between the observation point and the imaging unit 110 is maintained to be constant, for example, even if the imaging unit 110 is moved, vivid captured images can be provided to the operator at all times, without losing the focus, and thus convenience of the operator can be further improved.

Note that a functional configuration of the medical observation device 50 can be substantially the same as that of the medical observation device 30 according to the second embodiment shown in FIG. 8. In the medical observation device 50, however, the parallelogrammic link mechanism 640 corresponds to the active rotary shaft part 370, not to the passive rotary shaft part 160. In addition, the driving control unit 394 of the control unit 390 performs control similar to that in the second embodiment on the rotary shaft parts 420 and 430 in the point lock mode, i.e., driving control to cause the observation point to be positioned on the optical axis of the imaging unit 110 at all times, and control over driving of the parallelogrammic link mechanism 640 such that the distance between the observation point and the imaging unit 110 is maintained to be constant. For example, the driving control unit 394 computes a control amount for driving the parallelogrammic link mechanism 640 such that the distance between the observation point and the imaging unit 110 is maintained to be constant as a torque value based on the three-dimensional position information of the observation point at the time point at which the point lock operation is started, which is provided from the observation point position computation unit 193, and information regarding a state of the arm (i.e., a position and attitude of the holding unit) during the point lock operation, which is provided from the arm-state acquisition unit 192. Then, the driving control unit 394 drives the actuator 375 of the parallelogrammic link mechanism 640 to realize the torque value. Note that a generally used force control theory, for example, can be applied to the driving control unit 394 to compute the control amount.

The configuration of the third embodiment with the increased number of active shafts in comparison to the configuration shown in the second embodiment has been described so far. The third embodiment, however, is not limited thereto. For example, a medical observation device according to the third embodiment may be configured by providing an actuator in the parallelogrammic link mechanism 240 in the configuration of the medical observation device 10 according to the first embodiment shown in FIG. 2. In this case, the O2 shaft, the O3 shaft, and the O4 shaft act as active shafts likewise, and a point lock operation in which a distance between an observation point and the imaging unit 110 is controlled as described above can be realized. However, when the configuration of the medical observation device 10 according to the first embodiment is changed such that the parallelogrammic link mechanism 240 functions as an active shaft, control over driving of a parallelogrammic link mechanism after movement can be executed through position control, similarly to the rotary shaft parts 220 and 230 which correspond to other active shafts. In this case, a control amount for driving the parallelogrammic link mechanism such that a distance between the observation point and the imaging unit 110 is maintained to be constant can be computed as a value of a rotation angle of the parallelogrammic link mechanism by using, for example, a general position control technique.

<p style="text-align: center">5. Modified Examples</p>

A few modified examples of the first to third embodiments described above will be described.
(5-1. Modified Example in which Imaging Unit has AF Function)

First, a modified example in which an imaging unit has an auto focus (AF) function will be described. Here, a case in which the imaging unit 110 of the medical observation device 10 according to the first embodiment shown in FIG. 2 has the AF function will be described as an example.

As described in (2. First embodiment) above, the imaging unit 110 can perform the point lock operation by controlling the O2 shaft and the O3 shaft such that they perform active driving among the rotary shafts provided in the holding unit 120 in the first embodiment. In this manner, since the point lock operation of the first embodiment is performed through control over driving of the O2 shaft and the O3 shaft, a distance between the observation point and the imaging unit 110 is not necessarily constant even though tilting movement of the imaging unit 110 is controlled.

On the other hand, there are cases of surgical operations in which treatment such as cutting or grinding hard tissues such as bones is performed using, for example, chisels or hammers. When such treatment is performed, it is necessary to secure a relatively wide work space between an observation point (i.e., an operation site) and the imaging unit 110, and thus it is necessary to perform manipulation of moving the imaging unit 110 away from the observation point with the point lock operation continuing.

Figure 10:
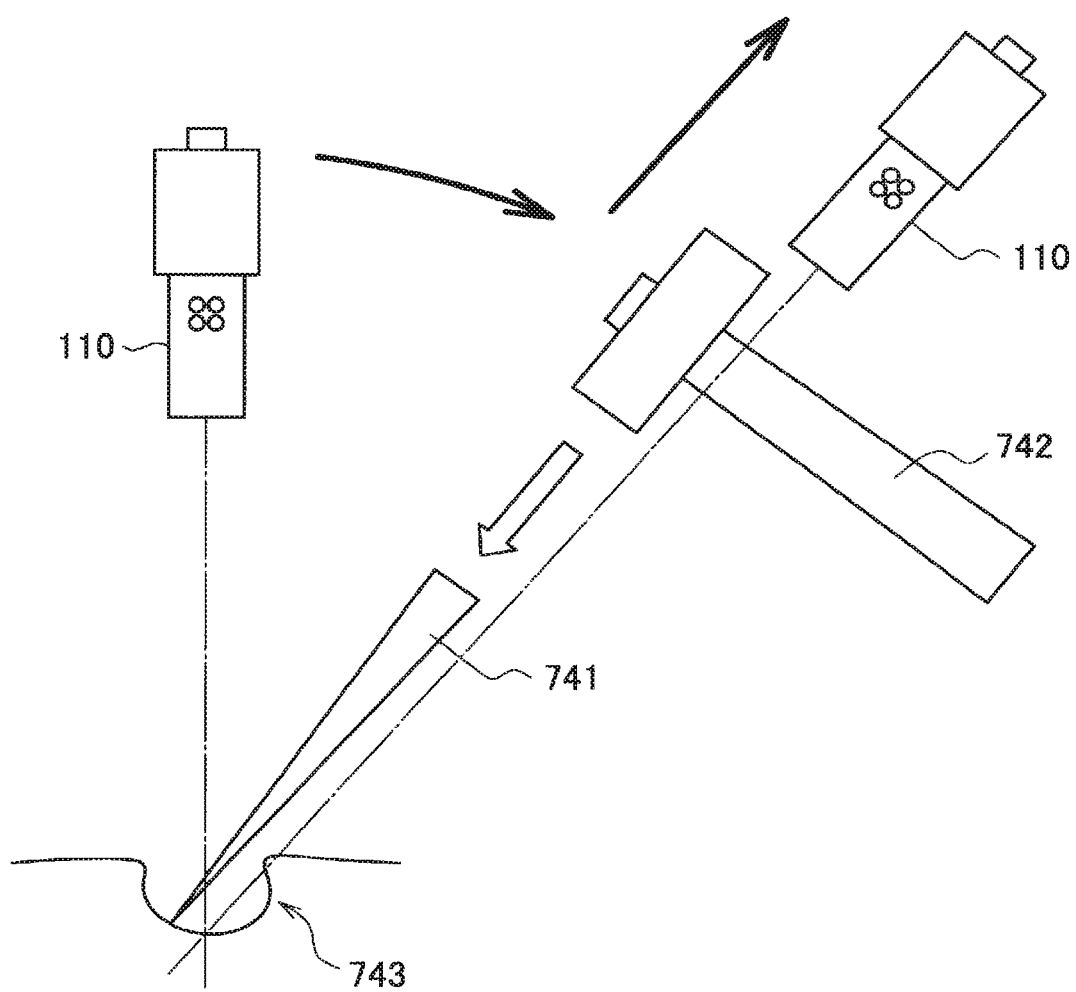
FIG. 10 is a diagram schematically showing manipulation of removing an imaging unit away from an observation point in order to secure a work space.

FIG. 10 is a diagram schematically showing manipulation of moving the imaging unit 110 away from an observation point in order to secure a work space. As shown in FIG. 10, when treatment is performed on the observation point 743 (an operation site 743) using a chisel 741 and a hammer 742, the imaging unit 110 can be tilted moved, and further manipulation of moving the imaging unit 110 away from the observation point 743 can be performed with the point lock operation continuing, i.e., with the observation point 743 fixed.

Here, a focal length of the imaging unit 110 is adjusted such that, for example, a position of the imaging unit 110 before movement coincides with the observation point 743. Thus, if the distance between the imaging unit 110 and the observation point 743 is changed, the focus is off, and thus it is not possible to perform normal observation on the observation point 743.

Thus, a focal length is adjusted when the imaging unit 110 has the AF function in the present modified example, for example, while the point lock SW 154 is being pressed (i.e., during a point lock operation) such that the focus of the imaging unit 110 is on the observation point 743 at all times due to the AF function. Accordingly, even when a distance between the imaging unit 110 and the observation point 743 is changed in the point lock operation, vivid captured images of the observation point 743 are provided to the operator at all times, and thus convenience of the operator can be improved.

Here, the time at which the operator actually performs treatment is after the position of the imaging unit 110 is changed to observe the observation point 743 from a different direction in the point lock operation and then the mode transitions to the fixed mode. Thus, the AF function of the imaging unit 110 may be configured to be effective when it is triggered by releasing the point lock SW 154, rather than to effectively function during the point lock operation at all times. With this configuration, the focus of the imaging unit 110 is set to be on the observation point 743 at the same time as a transition from the point lock mode to the fixed mode, and thus, it is not necessary for the operator to manually adjust a focal length using the focus SW 152, a surgical operation can be executed more smoothly.

The modified example in which the imaging unit 110 has the AF function has been described. Note that, although the case in which the imaging unit 110 of the medical observation device 10 according to the first embodiment has the AF function has been described above as an example, the present modified example can exhibit a similar effect when the imaging unit 110 of the medical observation device 30 according to the second embodiment has the AF function.

(5-2. Modified Example in which Imaging Unit is Moved Using Force Control Based on Sensing of Stress)

Next, a modified example in which an imaging unit is moved using force control based on sensing of stress will be described. Here, a case in which the present modified example is applied to the medical observation device 30 according to the second embodiment shown in FIG. 6 will be described as an example.

As described in (3. Second embodiment) above, the force sensors 421 and 431 are provided in the rotary shaft parts 420 and 430 which correspond to the O2 shaft and the O3 shaft in the holding unit 320, and driving of the rotary shaft parts 420 and 430 is controlled through so-called force control in the all-free mode and the point lock mode based on detection values of the force sensors 421 and 431 in the second embodiment. In the embodiment described above, driving of the rotary shaft parts 420 and 430 is controlled in the all-free mode such that detection values of the force sensors 421 and 431 become substantially zero. By performing such control, the operator can manually move the imaging unit 110, feeling substantially no resistance in the all-free mode. In addition, driving of the rotary shaft parts 420 and 430 is controlled in the point lock mode to realize a point lock operation. However, control which can be realized through force control is not limited thereto. By performing different control to perform control over driving of the rotary shaft parts 420 and 430 using force control in the present modified example, convenience of a user can be further improved.

FIG. 11 is an illustrative diagram for describing movement of the imaging unit 110 to which the present modified example is applied. FIG. 11 shows a state in which the constituent elements on the front end side of the rotary shaft part 430 in the configuration of the medical observation device 30 shown in FIG. 6, i.e., the imaging unit 110, the rotary shaft parts 210, 420, and 430, and the arms 271 and 272, are extracted and viewed in the z axis direction. In addition, a display screen 751 of a display device on which an image captured by the imaging unit 110 is displayed is also illustrated.

It is assumed that, for example, at the time immediately after the all-free mode or the point lock mode is finished and transitions to the fixed mode, an operation site 753 (i.e., an observation point 753) to be treated deviates from the center 752 of the display screen 751 as shown in FIG. 11(a). In this case, an operator has to finely adjust the position of the imaging unit 110 within the x-y plane such that the operation site 753 substantially coincides with the center 752 of the display screen 751.

Here, according to the manipulation method of the second embodiment described in (3-2. Operation in use) above, the operator can change the operation mode of the holding unit 320 to the all-free mode, and finely adjust the position of the imaging unit 110. However, the captured image displayed on the display screen 751 can be an image enlarged at a predetermined magnification ratio. Thus, differently from the distance appearing on the display screen 751, a movement distance of the imaging unit 110 that is actually needed is likely to be about, for example, several millimeters (mm). Although the imaging unit 110 can be moved using very light force with substantially no resistance in the all-free mode, when it is desired to move the imaging unit 110 only a slight distance, it is not possible to say that the all-free mode necessarily provides an optimum manipulation property.

Thus, when an operator exerts an external force whose value is greater than a predetermined value to move the imaging unit 110 in the fixed mode in the present modified example, driving of the rotary shaft parts 420 and 430 is controlled such that the imaging unit 110 is moved in the direction of the external force while a predetermined level of resistance is imparted to a hand of the operator. For example, as shown in FIG. 11 (b), if an operator exerts external force F to move the imaging unit 110, the external force F can be detected by the force sensors 421 and 431 as stress values f1 and f2 loaded on the rotary shaft parts 420 and 430. The controller 140 can compute the magnitude of the loaded external force F by combining the detected stress values f1 and f2. Furthermore, the controller 140 can compute the direction in which the external force F is loaded using the ratio between the stress values f1 and f2.

When the computed magnitude of the external force F is greater than a predetermined value, the controller 140 controls driving of the actuators 423 and 433 such that the imaging unit 110 is moved in the direction of the external force, giving a certain level of resistance to the hand of the operator while feeding detection values of the force sensors 421 and 431 and the encoders 422 and 432 back when necessary. The rotary shaft parts 420 and 430 are rotary shaft parts which correspond respectively to the O2 shaft and the O3 shaft which are two shafts orthogonal to the optical axis of the imaging unit 110, and thus by appropriately controlling driving of the rotary shaft parts 420 and 430, movement of the imaging unit 110 within the x-y plane can be controlled. Here, the controller 140 executes the driving control only while the operator imposes external force, and controls driving of the rotary shaft parts 420 and 430 such that the imaging unit 110 stops at the position at which the operator stops loading external force when the loading is performed. Accordingly, the operator can move the imaging unit 110 while feeling the certain level of resistance, and if he or she stops the manipulation of moving the imaging unit, the imaging unit 110 can stop at the current position. Therefore, manipulation of moving the imaging unit 110 only a slight distance can be executed more smoothly. Note that, since the control over driving of the rotary shaft parts 420 and 430 described above can be realized by applying, for example, a general force control theory thereto, detailed description thereof will be omitted.

Here, there is a possibility of a certain level of resistance being given to the operator when he or she manually moves the imaging unit 110 as in the present modified example by employing for example, a configuration in which light friction is mechanically created on rotation movement of the rotary shaft parts 420 and 430. However, when such mechanical friction is used, a stick-slip phenomenon caused by a difference between a coefficient of static friction and a coefficient of dynamic friction occurs, and thus there is concern of difficulty in smoothly moving the imaging unit 110. In addition, since movement of the imaging unit 110 within the x-y plane can be realized as it is interlinked with rotation movement of the rotary shaft parts 420 and 430, when mechanical friction is thus used, there is a possibility of movement of the imaging unit 110 in the x axis direction and movement thereof in the y axis direction not being smoothly interlinking with each other, but turning into step-like movement.

On the other hand, according to the present modified example, by controlling the actuators 423 and 433, the operator is allowed to move the imaging unit 110 while feeling a certain level of resistance. Since outputs of the actuators 423 and 433 can be interlinked and continuously changed, the resistance given to the operator does not drastically change, and the imaging unit 110 can be linearly moved within the x-y plane.

The modified example in which the imaging unit 110 is moved through force control based on sensing of stress has been described above. According to the present modified example, convenience of the operator can be further improved by performing different types of control to move the imaging unit 110 using the force control as described above. Note that, although the case in which the present modified example is applied to the medical observation device 30 according to the second embodiment has been described above as an example, the present modified example can also be applied to a medical observation device having another configuration as long as a force sensor is provided in a rotary shaft part which is a control target and the rotary shaft part is driven through force control. For example, the present modified example may be applied to the medical observation device 50 according to the third embodiment described above. In this case, based on stress detected by the force sensors 421, 431, and 641 of the rotary shaft parts 420 and 430, and the parallelogrammic link mechanism 640 shown in FIG. 9, driving of the rotary shaft parts 420 and 430, and the parallelogrammic link mechanism 640 is controlled such that the imaging unit 110 is moved in a state in which a certain level of resistance is given in a direction of loaded external force, and similar control over three-dimensional movement of the imaging unit 110 can be executed.

6. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Note that each of the embodiments and modified examples described above can be combined with each other within a possible range. For example, some of the active shafts may be configured as active shafts whose driving is controlled through position control (for example, the rotary shaft parts 220 and 230 shown in FIG. 2), and the remaining active shafts may be configured as active shafts whose driving is controlled through force control (for example, the rotary shaft parts 420 and 430 shown in FIG. 6). In this case, by appropriately combining position control and force control to control driving of the active shafts, control over driving of the holding unit similar to that in the embodiments and modified examples can be performed.

Additionally, the present technology may also be configured as below.

(1)

A medical observation device including:

an imaging unit configured to photograph an image of an operation site;

a holding unit configured to be connected with the imaging unit and have rotary shafts which are operable with at least six degrees of freedom, wherein, among the rotary shafts, at least two shafts are active shafts whose driving is controlled based on states of the rotary shafts, and at least one shaft is a passive shaft which is rotated according to direct external manipulation accompanying contact.

(2)

The medical observation device according to (1), wherein a position and an attitude of the imaging unit are controlled by controlling driving of the active shafts based on a predetermined condition.

(3)

The medical observation device according to (1) or (2), wherein, when the imaging unit is moved, driving of the active shafts is controlled such that an observation point with respect to the imaging unit after movement coincides with the observation point with respect to the imaging unit before movement and the observation point is positioned on the optical axis of the imaging unit.

(4)

The medical observation device according to any one of (1) to (3), wherein the active shafts include at least two rotary shafts which can decide a tilt of the imaging unit.

(5)

The medical observation device according to any one of (1) to (4), wherein the active shafts include a first rotary shaft which is orthogonal to an optical axis of the imaging unit and a second rotary shaft which is orthogonal to the optical axis and the first rotary shaft.

(6)

The medical observation device according to any one of (1) to (5), wherein the holding unit is a balance arm having a counterweight.

(7)

The medical observation device according to any one of (1) to (6), wherein the rotary shafts have state detection units configured to detect states of the rotary shafts, the rotary shafts which function as the active shafts further have actuators configured to drive rotation of the rotary shafts, and driving of the actuators of the active shafts is controlled based on states of the respective rotary shafts detected by the state detection units.

(8)

The medical observation device according to (7), wherein the state detection units include encoders configured to detect rotation angles of the rotary shafts, and driving of the actuators of the active shafts is controlled based on rotation angles of the respective rotary shafts detected by the encoders.

(9)

The medical observation device according to (8), wherein the state detection units provided in the active shafts further include force sensors configured to detect external force loaded at least on the active shafts, and driving of the actuators of the active shafts is controlled based on rotation angles of the respective rotary shaft detected by the encoders and stress values of the respective active shafts detected by the force sensors.

(10)

The medical observation device according to any one of (1) to (9), wherein the active shafts include at least two rotary shafts which can decide a tilt of the imaging unit and one rotary shaft which can decide a distance between the imaging unit and an observation point, and when the imaging unit is moved, driving of the active shafts is controlled such that the observation point with respect to the imaging unit after movement coincides with the observation point with respect to the imaging unit before movement and a distance between the imaging unit and the observation point is maintained to be constant.

(11)

The medical observation device according to any one of (1) to (10), wherein an operation mode of the holding unit is capable of being switched to at least one of a point lock mode in which driving of the active shafts is controlled such that an observation point with respect to the imaging unit after movement coincides with the observation point with respect to the imaging unit before movement when the imaging unit is moved, and a fixed mode in which rotation of the rotary shafts is fixed.

(12)

The medical observation device according to (11),
wherein the imaging unit has an AF function, and
the AF function works at all times so that a focus is on the observation point when the imaging unit is moved in the point lock mode.

(13)

The medical observation device according to (11),
wherein the imaging unit has an AF function, and
the AF function works so that a focus is on the observation point when a mode transitions from the point lock mode to the fixed mode.

(14)

The medical observation device according to (1) or (2),
wherein the active shafts include a first rotary shaft which is orthogonal to an optical axis of the imaging unit and a second rotary shaft which is orthogonal to the optical axis and the first rotary shaft, the first and second rotary shafts have encoders configured to detect rotation angles of the first and second rotary shafts, force sensors configured to detect external force loaded at least on the first and second rotary shafts, and actuators configured to drive rotation of the first and second rotary shafts, and driving of the actuators of the active shafts is controlled based on detection values of the encoders and the force sensors of the active shafts such that, when external force is loaded to move the imaging unit, the imaging unit is moved in a direction of the external force detected based on detection values of the force sensors of the first and second rotary shafts while the external force is being loaded.

(15)

A medical observation device including:

an imaging unit configured to photograph an image of an operation site; and a holding unit configured to be connected with the imaging unit and have rotary shafts which are operable with at least six degrees of freedom, wherein, among the rotary shafts, at least two shafts, which are a first rotary shaft which is orthogonal to an optical axis of the imaging unit and a second rotary shaft which is orthogonal to the optical axis and the first rotary shaft, are active shafts whose driving is controlled based on states of the rotary shafts, and at least one shaft is a passive shaft which is rotated according to direct external manipulation accompanying contact, and the first and second rotary shafts have encoders configured to detect rotation angles of the first and second rotary shafts, force sensors configured to detect external force loaded at least on the first and second rotary shafts, and actuators configured to drive rotation of the first and second rotary shafts.

(16)

The medical observation device according to (15), wherein driving of the actuators is controlled based on detection values of the encoders and the force sensors such that, when external force is loaded to move the imaging unit, the imaging unit is moved in a direction of the external force detected based on detection values of the force sensors of the first and second rotary shafts while the external force is being loaded.

REFERENCE SIGNS LIST 10, 30, 50 medical observation device
110 imaging unit
120, 320, 520 holding unit (arm unit)
130 base
140 controller
160 passive rotary shaft part
161, 171, 371 state detection unit
163, 173, 374 operation unit
170, 370 active rotary shaft part
180 storage unit
190, 390 control unit
191, 391 operation mode control unit
192 arm-state acquisition unit
193 observation point position computation unit
194, 394 driving control unit
210, 220, 230, 250, 260, 420, 430 rotary shaft part
240, 640 parallelogrammic link mechanism
211, 221, 231, 251, 261, 291 brake
119, 212, 222, 232, 252, 262, 292, 422, 432, 642 encoder
118, 223, 233, 423, 433, 643 actuator
280 counterweight
421, 431, 641 force sensor
241, 242, 243, 244, 271, 272, 273, 274 arm
245, 246, 247, 248 shaft bearing

The invention claimed is:

1. A medical observation device comprising:
an imager to photograph an image of an operation site;
a holder to be coupled with the imager and that includes rotary shafts which are operable with at least six degrees of freedom, wherein, among the rotary shafts, at least two of the rotary shafts are motorized shafts and at least one of the rotary shafts is a non-motorized shaft which is rotated according to direct external manipulation accompanying contact; and
processing circuitry configured to control driving of the motorized shafts based on states of the rotary shafts such that the direct external manipulation changes a state of the at least one non-motorized shaft and a rotation of the motorized shafts are controlled by the processing circuitry based on the state of the at least one non-motorized shaft to modify an imaging direction.

2. The medical observation device according to claim 1, wherein the processing circuitry is configured to control a position and an attitude of the imager by controlling driving of the motorized shafts based on a predetermined condition which includes the state of the at least one non-motorized shaft.

3. The medical observation device according to claim 2, wherein, when the imager is moved, the processing circuitry is configured to control driving of the motorized shafts such that an observation point with respect to the imager after movement coincides with the observation point with respect to the imager before movement.

4. The medical observation device according to claim 3, wherein the motorized shafts include at least two rotary shafts which are operable to tilt the imager.

5. The medical observation device according to claim 4, wherein the motorized shafts include a first rotary shaft which is orthogonal to an optical axis of the imager and a second rotary shaft which is orthogonal to the optical axis and the first rotary shaft.

6. The medical observation device according to claim 1, wherein the holder is a balance arm having a counterweight.

7. The medical observation device according to claim 1, wherein the rotary shafts have state detectors to detect states of the rotary shafts,
the rotary shafts which function as the motorized shafts further include actuators to drive rotation of the rotary shafts, and
the processing circuitry is configured to control driving of the actuators of the motorized shafts based on the states of the respective rotary shafts detected by the state detectors.

8. The medical observation device according to claim 7, wherein the state detectors include encoders to detect rotation angles of the shafts, and
the processing circuitry is configured to control driving of the actuators of the motorized shafts based on the rotation angles of the respective rotary shafts detected by the encoders.

9. The medical observation device according to claim 8, wherein the state detectors provided in the motorized shafts further include force sensors to detect external force loaded at least on the motorized shafts, and
the processing circuitry is configured to control driving of the actuators of the motorized shafts based on the rotation angles of the respective rotary shaft detected by the encoders and stress values of the respective motorized shafts detected by the force sensors.

10. The medical observation device according to claim 1, wherein the motorized shafts include at least two rotary shafts which are operable to tilt the imager and one rotary shaft which is operable to adjust a distance between the imager and an observation point, and
when the imager is moved, the processing circuitry is configured to control driving of the motorized shafts such that the observation point is positioned on an optical axis of the imager so that the observation point with respect to the imager after movement coincides with the observation point with respect to the imager before movement and a distance between the imager and the observation point is maintained to be constant.

11. The medical observation device according to claim 1, wherein an operation mode of the holder is switchable to at least one of
a point lock mode in which the processing circuitry is configured to control driving of the motorized shafts such that an observation point with respect to the imager after movement coincides with the observation point with respect to the imager before movement when the imager is moved, and
a fixed mode in which rotation of the rotary shafts is fixed.

12. The medical observation device according to claim 11, wherein the imager includes an AF (auto focus) function, and
the AF function works at all times so that a focus is on the observation point when the imager is moved in the point lock mode.

13. The medical observation device according to claim 11, wherein the imager includes an AF (auto focus) function, and
the AF function works so that a focus is on the observation point when a mode transitions from the point lock mode to the fixed mode.

14. The medical observation device according to claim 1, wherein the motorized shafts include a first rotary shaft which is orthogonal to an optical axis of the imager and a second rotary shaft which is orthogonal to the optical axis and the first rotary shaft,
the first and second rotary shafts include encoders to detect rotation angles of the first and second rotary shafts, force sensors to detect external force loaded at least on the first and second rotary shafts, and actuators to drive rotation of the first and second rotary shafts, and
the processing circuitry is configured to control driving of the actuators of the motorized shafts based on detection values of the encoders and the force sensors of the motorized shafts such that, when external force is loaded to move the imager, the imager is moved in a direction of the external force detected based on detection values of the force sensors of the first and second rotary shafts while the external force is being loaded.

15. A medical observation device comprising:
an imager to photograph an image of an operation site; and
a holder to be coupled with the imager and that includes rotary shafts which are operable with at least six degrees of freedom, wherein, among the rotary shafts, at least two of the rotary shafts, which are a first rotary shaft which is orthogonal to an optical axis of the imager and a second rotary shaft which is orthogonal to the optical axis and the first rotary shaft, are motorized shafts, and at least one of the rotary shafts is a non-motorized shaft which is rotated according to direct external manipulation accompanying contact; and
processing circuitry configured to control driving of the motorized shafts based on states of the rotary shafts such that the direct external manipulation changes a state of the at least one non-motorized shaft and a rotation of the motorized shafts are controlled by the processing circuitry based on the state of the at least one non-motorized shaft to modify an imaging direction, wherein
the first and second rotary shafts include encoders to detect rotation angles of the first and second rotary shafts, force sensors to detect external force loaded at least on the first and second rotary shafts, and actuators to drive rotation of the first and second rotary shafts.

16. The medical observation device according to claim 15, wherein the processing circuitry is configured to control driving of the actuators based on detection values of the encoders and the force sensors such that, when external force is loaded to move the imager, the imager is moved in a direction of the external force detected based on detection values of the force sensors of the first and second rotary shafts while the external force is being loaded.

17. The medical observation device according to claim 1, wherein the holder includes only two motorized shafts among the rotary shafts.

18. A medical observation device comprising:
an imager to photograph an image of an operation site;
a holder to be coupled with the imager and that includes rotary shafts which are operable with at least six degrees of freedom, wherein, among the rotary shafts, at least two of the rotary shafts are active shafts and at least one of the rotary shafts is a passive shaft which is rotated according to direct external manipulation accompanying contact; and processing circuitry configured to control driving of the active shafts based on states of the rotary shafts such that the direct external manipulation changes a state of the at least one passive shaft and a rotation of the active shafts are controlled by the processing circuitry based on the state of the at least one passive shaft to modify an imaging direction.

19. The medical observation device according to claim 18, wherein the processing circuitry is configured to control a position and an attitude of the imager by controlling driving of the active shafts based on a predetermined condition which includes the state of the at least one passive shaft.

20. The medical observation device according to claim 19, wherein, when the imager is moved, the processing circuitry is configured to control driving of the motorized shafts such that an observation point with respect to the imager after movement coincides with the observation point with respect to the imager before movement.

* * * * *